US007358361B2

(12) United States Patent
Sanders et al.

(10) Patent No.: US 7,358,361 B2
(45) Date of Patent: Apr. 15, 2008

(54) BIOPHOSPHONATE COMPOUNDS AND METHODS FOR BONE RESORPTION DISEASES, CANCER, BONE PAIN, IMMUNE DISORDERS, AND INFECTIOUS DISEASES

(75) Inventors: John M. Sanders, Champaign, IL (US); Yongcheng Song, Urbana, IL (US); Julian M. W. Chan, Boston, MA (US); Eric Oldfield, Champaign, IL (US); Yonghui Zhang, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 11/245,612

(22) Filed: Oct. 7, 2005

(65) Prior Publication Data

US 2006/0079487 A1 Apr. 13, 2006

Related U.S. Application Data

(60) Provisional application No. 60/617,108, filed on Oct. 8, 2004.

(51) Int. Cl.
*C07F 9/38* (2006.01)
*C07F 9/28* (2006.01)
(52) U.S. Cl. .......................... 546/22; 546/23; 546/24; 546/25
(58) Field of Classification Search .................. 514/89, 514/82, 358, 336, 311; 546/22, 23, 24, 25
See application file for complete search history.

(56) References Cited

U.S. PATENT DOCUMENTS

| 4,621,077 | A | 11/1986 | Rosini et al. |
| 4,711,880 | A | 12/1987 | Stahl et al. |
| 4,777,163 | A | 10/1988 | Bosies et al. |
| 4,859,472 | A | 8/1989 | Demmer et al. |
| 4,871,720 | A | 10/1989 | Jaeggi |
| 4,927,814 | A | 5/1990 | Gall et al. |
| 4,939,130 | A | 7/1990 | Jaeggi et al. |
| 5,227,506 | A | 7/1993 | Saari et al. |
| 5,462,932 | A | 10/1995 | Brenner et al. |
| 5,583,122 | A | 12/1996 | Benedict et al. |
| 5,756,423 | A | 5/1998 | Cromartie et al. |
| 5,994,329 | A | 11/1999 | Daifotis et al. |
| 6,015,801 | A | 1/2000 | Daifotis et al. |
| 6,096,342 | A | 8/2000 | Dansereau et al. |
| 6,143,326 | A | 11/2000 | Mockel et al. |
| 6,165,513 | A | 12/2000 | Dansereau et al. |
| 6,225,294 | B1 | 5/2001 | Daifotis et al. |
| 6,294,196 | B1 | 9/2001 | Gabel et al. |
| 6,372,728 | B1 | 4/2002 | Ungell |
| 6,410,520 | B2 | 6/2002 | Cazer et al. |
| 6,544,967 | B2 | 4/2003 | Daifotis et al. |
| 6,562,974 | B2 | 5/2003 | Cazer et al. |
| 6,638,920 | B2 | 10/2003 | Thompson |
| 6,753,324 | B2 | 6/2004 | Jomaa |

FOREIGN PATENT DOCUMENTS

| DE | 19859668 | 12/1999 |
| JP | 55098193 | 7/1980 |
| WO | 95/34207 | 12/1995 |
| WO | WO 03/075741 | 9/2003 |
| WO | WO 03/097655 | 11/2003 |
| WO | WO 2004/024165 | 3/2004 |
| WO | WO 2004/050096 | 6/2004 |

OTHER PUBLICATIONS

Alfer'ev IS et al., Reactions of vinylidenediphosphonic acid with nucleophiles. 1. Addition of aliphatic amines, Izvestiay Akademii Nauk SSSR, Seriya Khimicheskaya, No. 12, pp. 2802-2806, Dec. 1983 [Bull. Acad. Sci. USSR, Div. Chem. Sci., 1983, 32:2515 (Engl. Transl.)].
Alfer'ev IS et al., Izv. Akad. Nauk SSSR, Ser. Khim., 1984:1122 [Bull. Acad. Sci. USSR, Div. Chem. Sci., 1984, 33:1031 (Engl. Transl.)].
Alfer'ev, I. S. et al., Reactions of vinylidenediphosphonic acid with nucleophiles. 5. Addition of heterocyclic amines and trimethylamine to vinylidenediphosphonic acid; Aug. 1994, Russian Chemical Bulletin 44(8):1528-1530 (translated from Izvestiya Akademii Nauk, Seriya Khimicheskaya 8:1590-1592, 1995).
Bergstrom, J. D. et al., Alendronate is a specific, nanomolar inhibitor of farnesyl diphosphate synthase, Arch. Biochem. Biophys. 373:231-241, 2000.
Bundgaard, H., "Design of Prodrugs," In: *Methods in Ezymology*, K. Widder et al., Eds., Academic Press, Elsevier, pp. 309-396, 1985.
Bundgaard, H., Design and Application of Prodrugs, Chapter 5, In: A Textbook of Drug Design and Development, Krosgaard-Larsen et al. (eds.), pp. 113-191, 1991.
Bundgaard, H., (C) Means to enhance penetration. (1) Prodrugs as a means to improve the delivery of peptide drugs, Advanced Drug Delivery Reviews 8:1-38, 1992.

(Continued)

*Primary Examiner*—Charanjit S. Aulakh
(74) *Attorney, Agent, or Firm*—Greenlee, Winner and Sullivan P.C.

(57) ABSTRACT

Bisphosphonate compounds and related methods of making and using are disclosed, including pyridinium-1-yl, quinolinium-1-yl, and related compounds. The activity of compounds is disclosed in the context of functional assays such as *Leishmania major* farnesyl diphosphate synthase (FPPS) inhibition, *Dictyostelium discoideum* growth inhibition, human gamma delta T cell activation, and bone resorption. The applicability of bisphosphonate compounds in the context of parasitic infections, for example against trypanosomes, is disclosed. Further potential applications of the invention are disclosed regarding the treatment of one or more conditions such as bone resorption disorders, cancer, bone pain, infectious diseases, and in immunotherapy.

12 Claims, 9 Drawing Sheets

OTHER PUBLICATIONS

Caraglia, M. et al., The farnesyl transferase inhibitor R115777 (Zarnestra) synergistically enhances growth inhibition and apoptosis induced on epidermoid cancer cells by Zoledronic acid (Zometa) and Pamidronate, Oncogene 23:6900-6913, 2004.

Cromartie, T. H. et al., The discovery of a novel site of action for herbicidal bisphosphonates, Pesticide Biochem. Phys. 63:114-126, 1999.

Dawson, N. A., Therapeutic benefit of bisphosphonates in the management of prostate cancer-related bone disease, Expert. Opin. Pharmacother. 4(5):705-716, 2003.

De Cock et al., Cost-effectiveness of oral ibandronate versus IV zoledronic acid or IV pamidronate for bone metastases in patients receiving oral hormonal therapy for breast cancer in the United Kingdom, Clin. Ther. 27(8):1295-1310, 2005.

Dunfor, J. E. et al., Structure-activity relationships for inhibition of farnesyl diphosphate synthase in vitro and inhibition of bone resorption in vivo by nitrogen-containing bisphosphonates, J. Pharmacol. Exp. Ther. 296(2):235-242, 2001.

Fisher, J. E. et al., Alendronate mechanism of action: geranylgeraniol, an intermediate in the mevalonate pathway, prevents inhibition of osteoclast formation, bone resorption, and kinase activation in vitro, Proc. Natl. Acad. Sci. USA 96:133-138, 1999.

Forsea, A.-M. et al., Nitrogen-containing bisphosphonates inhibit cell cycle progression in human melanoma cells, Br. Jr. Cancer 91:803-810, 2004.

Garzoni, L. R. et al., Selective in vitro effects of the farnesyl pyrophosphate synthase inhibitor risedronate on Trypanosoma cruzi, Intl. J. Antimicrobial Agents 23:273-285, 2004.

Garzoni, L. R. et al., Antiparasitic activity of risedronate in a murine model of acute Chagas' disease, Intl. J. Antimicrobial Agents 23:286-290, 2004.

Ghosh, S. et al., Effects of bisphosphonates on the growth of Entamoeba histolytica and Plasmodium species in vitro and in vivo, J. Med. Chem. 47:175-187, 2004.

Gordon, D. H., Efficacy and safety of intravenous bisphosphonates for patients with breast cancer metastatic to bone: a review of randomized, double-blind, phase III trials, Clin Breast Cancer. 6(2):125-31, 2005.

Green, J. R., Chemical and biological prerequisites for novel bisphosphonate molecules: results of comparative preclinical studies, Semin Oncol. 28(2 Suppl 6):4-10, 2001.

Green, J.R., Bisphosphonates: Preclinical Review, The Oncologist 9(suppl 4):3-13, 2004.

Grove, J. E. et al., The intracellular target for the antiresorptive aminobisphosphonate drugs in Dictyostelium discoideium is the enzyme farnesyl diphosphate synthase, J. Bone Miner. Res. 15(5):971-981, 2000.

Heidenreich et al., Ibandronate in metastatic bone pain, Semin. Oncol. 31:67-72, 2004.

Jagdev, S. P. et al., The bisphosphonate, zoledronic acid, induces apoptosis of breast cancer cells: evidence for synergy with paclitaxel, Br J Cancer 84(8):1126-1134, 2001.

Kato, Y. et al., Targeting of tumor cells for human $\gamma\delta$ T cells by nonpeptide antigens, J. Immunol. 167:5092-5098, 2001.

Keller, R. K. et al., Mechanism of aminobisphosphonate action: characterization of alendronate inhibition of the isoprenoid pathway, Biochem. Biophys. Res. Commun. 266:560-563, 1999.

Kotsikorou, E. et al., A quantitative structure-activity relationship and pharmacophore modeling investigation of aryl-X and heterocyclic bisphosphonates as bone resorption agents, J. Med. Chem. 46(14):2932-2944, 2003.

Kotsikorou, E. et al., Bisphosphonate inhibition of the exopolyphosphatase activity of the Trypanosoma brucei soluble vacuolar pyrophosphatase, J. Med. Chem. 48:6128-6139, 2005.

Krapcho, A. P. et al., Synthesis of regioisomeric difluoro- and 8-chloro-9-fluorobenz[g] isoquinoline-5, 10-diones and SNAr displacements studies by diamines: bis(aminoalkyl) aminobenz[g]isoquinoline-5,10-diones, J. Fluorine Chem. 90:139-147, 1998.

Kunzmann, V. et al., Stimulation of $\gamma\delta$ T cells by aminobisphosphonates and induction of antiplasma cell activity in multiple myeloma, Blood 96(2):384-392, 2000.

Luckman, S. P. et al., Nitrogen-containing bisphosphonates inhibit the mevalonate pathway and prevent post-translational prenylation of GTP-binding proteins, including Ras, J. Bone Miner. Res. 13(4):581-589, 1998.

Martin, M. B. et al., Bisphosphonates inhibit the growth of Trypanosoma brucei, Trypanosoma cruzi, Leishmania donovani, Toxoplasma gondii, and Plasmodium falciparum: A potential route to chemotherapy, J. Med. Chem. 44:909-916, 2001.

Martin, M. B. et al., Activity of bisphosphonates against Trypanosoma brucei rhodesiense, J. Med. Chem. 45:2904-2914, 2002.

Miyaura, N. et al., The palladium-catalyzed cross-coupling reaction of phenylboronic acid with haloarenes in the presence of bases, Synth. Commun. 11:513-519, 1981.

Montalvetti, A. et al., Bisphosphonates are potent inhibitors of Trypanosoma cruzi farnesyl pryrophosphate synthase, J. Biol. Chem. 276(36):33930-33937, 2001.

Moreno, B. et al., $^{31}$P NMR of apicomplexans and the effects of risedronate on Cryptosporidium parvum growth, Biochem. Biophys. Res. Commun. 284:632-637, 2001.

Nielsen, N. M. et al., Glycolamide esters as biolabile prodrugs of carboxylic acid agents: Synthesis of stability, bioconversion, and physicochemical properties, J. Pharmaceutical Sciences, 77(4):285-298, 1988.

Nogrady, Medicinal Chemistry A Biochemical Approach, Oxford University Press, New York, pp. 388-394, 1985.

Rodriguez, N. et al., Radical cure of experimental cutaneous leishmaniasis by the bisphosphonate pamidronate, J. Infect. Dis. 186:138-140, 2002.

Rogers, M. J. et al., Inhibitory effects of bisphosphonates on growth of amoebae of the cellular slime mold Dictyostelium discoideum, J. Bone Miner, Res. 9(7):1029-1039, 1994.

Rosen, L. S. et al., Zoledronic acid is superior to pamidronate for the treatment of bone metastases in breast carcinoma patients with at least one osteolytic lesion, Cancer 100:36-43, 2004.

Salomo, M. et al., How myeloma cells escape bisphosphonate-mediated killing: development of specific resistance with preserved sensitivity to conventional chemotherapeutics, Br. J. Haematology 122:202-210, 2003.

Sambrook, P. N. et al., Alendronate produces greater effects than raloxifene on bone density and bone turnover in postmenopausal women with low bone density: results of EFFECT (EFficacy of FOSAMAX versus EVISTA Comparison Trial) International, J. Intern. Med. 255:503-511, 2004.

Sanders, J. M. et al., 3-D QSAR investigations of the inhibition of Leishmania major farnesyl pyrophosphate synthase by bisphosphate, J. Med. Chem. 46:5171-5183, 2003.

Sanders, J. M. et al., Quantitative structure-activity relationships for $\gamma\delta$ T cell activation by bisphosphonates, J. Med. Chem. 47:375-384, 2004.

Sanders, J. M. et al., Pyridinium-1-yl bisphosphonates are potent inhibitors of farnesyl diphosphate synthase and bone resorption, J. Med. Chem. 48:2957-2963, 2005.

Thompson, K. et al., Statins prevent bisphosphonate-induced $\gamma\delta$ - T-cell proliferation and activation in vitro, J. Bone Miner. Res. 19(2):278-288, 2004.

van Beek, E. et al., Nitrogen-containing bisphosphonates inhibit isopentenyl pyrophosphate isomerase/farnesyl pyrophosphate synthase activity with relative potencies corresponding to their antiresorption potencies in vitro and in vivo, Biochem. Biophys. Res. Commun. 255:491-494, 1999.

van Beek, E. et al., Farnesyl pyrophosphate synthase is the molecular target of nitrogen-containing bisphosphonates, Biochem. Biophys. Res. Commun. 264:108-111, 1999.

van Beek, E. et al., The role of geranylgeranylation in bone resorption and its suppression by bisphosphonates in fetal bone explants in vitro: A clue to the mechanism of action of nitrogen-containing bisphosphonates, J. Bone Miner. Res. 14(5):722-729, 1999.

van Beek, E. R. et al., Differentiating the mechanisms of antiresorptive action of nitrogen containing bisphosphonates, Bone 33:805-811, 2003.

Vasireddy, S. et al., Patterns of pain in Paget's disease of bone and their outcomes on treatment with pamidronate, Clin. Rheumatol. 22:376-380, 2003.

Wang, L. et al., Antibacterial effect of human Vγ2Vδ2 T cells in vivo, J. Clin. Invest. 108(9):1349-1357, 2001.

Widler, L. et al., Highly potent geminal bisphosponates. From pamidronate disodium (Aredia) to zoledronic acid (Zometa), J Med Chem. 45(17):3721-3738, 2002.

Wilhelm, M. et al., γδ T cells for immune therapy of patients with lymphoid malignancies, Blood 102(1):200-206, 2003.

Yardley, V. et al., In vivo activities of fanesyl pyrophosphate synthase inhibitors against *Leishmania donovani* and *Toxoplasma gondii*, Antimicrob. Agents Chemother. 46(3):929-931, 2002.

Zhang, L. et al., A novel and practical synthesis of 3-unsubstituted indolizines, Synthesis 12:1733-1737, 2000.

D. Amin et al., "Bisphosphonates used for the treatment of bone disorders inhibit squalene synthase and cholesterol biosynthesis," Journal of Lipid Research 33:1657-1663, 1992.

PCT International Search Report, International Application No. PCT/US05/36425, Mar. 16, 2006, 3 pages.

V. J. Davisson et al., Phosphorylation of isoprenoid alcohols, J. Org. Chem. 51:4768-4779, 1986.

R. Ortmann et al., Acyloxyalky ester prodrugs of FR900098 with improved in vivo anti-malarial activity, Bioorganic & Medicinal Chemistry Letters 13:2163-2166, 2003.

J. J. Vepsalainen, Bisphosphonate prodrugs: A new synthetic strategy to tetraacyloxymethyl esters of methyllenebisphosphonates, Tetrahedron Letters 40:8491-8493, 1999.

1

2

3

4

5

6

Compounds C1 – C6.

Synthetic Routes

General synthetic routes

1. Preparation of substituted pyridine (if not commercially available)

R = aryl or alkyl
M = B, Zn, Sn, etc.

2a. Preparation of 1-hydroxy-2-(substitutedpyridinium-1-yl)ethyl-1,1-diphosphonic acid R = aryl or alkyl 2b. Preparation of 2-(substitutedpyridinium-1-yl)ethyl-1,1-diphosphonic acid R = aryl or alkyl 3. p-ketone or aldehyde analog of 300

Compounds C5 and C7-C18

BIOPHOSPHONATE COMPOUNDS AND METHODS FOR BONE RESORPTION DISEASES, CANCER, BONE PAIN, IMMUNE DISORDERS, AND INFECTIOUS DISEASES

CROSS-REFERENCES TO RELATED APPLICATIONS

This application claims the benefit of U.S. Provisional Patent Application 60/617,108 by Sanders et al., filed Oct. 8, 2004, which is incorporated by reference in entirety.

STATEMENT REGARDING FEDERALLY SPONSORED RESEARCH OR DEVELOPMENT

This invention was made, at least in part, with government support under Grant Nos. GM50694 and GM65307 awarded by the National Institutes of Health. The government has certain rights in the invention.

BACKGROUND OF THE INVENTION

Nitrogen-containing bisphosphonates such as pamidronate (Aredia®) C1; alendronate (Fosamax®) C2; risedronate (Actonel®) C3; and zoledronate (Zometa®) C4; shown in their zwitterionic forms in FIG. 1, represent an important class of drugs, currently used to treat osteoporosis, Paget's disease and hypercalcemia due to malignancy. See references 1-4. These compounds function primarily by inhibiting the enzyme farnesyl diphosphate synthase (FPPS) (references 5-12) resulting in decreased levels of protein prenylation in osteoclasts (references 13-15). Certain bisphosphonates have also been found to have anti-parasitic activity (references 16-25) and have been found to stimulate human γδ T cells (references 26-30); there is currently interest in their use as vaccines for a variety of B cell malignancies (reference 31).

Differences in substituents, however, can strongly influence the pharmacologic properties of such compounds (Green, 2001). Structural differences may also be significant in the potential expansion of therapies. For example, Bonefos (clodronate) is a bisphosphonate indicated for the treatment of tumor-induced osteolysis and hypercalcemia. It has been reported to increase survival and reduce the risk of bone metastasis in women with stage II/III breast cancer. This is noteworthy as approximately 70% of women who develop recurrence of breast cancer will experience bone metastasis, and breast cancer remains the leading cause of death among women aged 40 to 55 years.

For even second generation bisphosphonates, it is recognized that small changes of structure can lead to marked improvements in activity or function, for example in the inhibition of osteoclastic resorption potency (Widler et al., 2002). Therefore, there is great interest in the further development of alternative bisphosphonate compounds and the exploration of methods of use such as clinical applications.

SUMMARY OF THE INVENTION

The present invention surprisingly provides the first report of the synthesis and testing of a series of pyridinium-1-yl and related bisphosphonates. Bisphosphonate compounds of the invention can demonstrate activity in one or more contexts, including a farnesyl diphosphate synthase (FPPS) assay, a *D. discoideum* growth inhibition assay, a T cell activation assay, a bone resorption assay, the treatment of infectious disease, the treatment of a bone resorption clinical disorder, an immunotherapeutic treatment, the treatment of cancer, and the treatment of bone pain.

The invention broadly provides bisphosphonate compounds and related methods of making and using. The invention specifically provides compounds with an N-linkage including pyridinium-1-yl, quinolinium-1-yl, and related bisphosphonate compounds.

The following abbreviations are applicable. FPPS, farnesyl diphosphate synthase; $pIC_{50}/pEC_{50}$, negative log of $IC_{50}$ and $EC_{50}$, respectively, where $IC_{50}$ and $EC_{50}$ are the concentrations that produce half-maximal inhibition or activation, respectively; *L. major*, *Leishmania major*, *D. discoideum*, *Dictyostelium discoideum*; γδ T cells, gammadelta T cells. Compounds are optionally designated by a number or in some cases a number preceded by a letter to help distinguish a compound designation from a cardinal number, e.g. C1 is compound 1.

The following definitions are applicable.

Alkyl groups include straight-chain, branched and cyclic alkyl groups. Alkyl groups include those having from 1 to 20 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-20 carbon atoms. Cyclic alkyl groups include those having one or more rings. Cyclic alkyl groups include those having a 3-, 4-, 5-, 6-, 7-, 8-, 9- or 10-member carbon ring and particularly those having a 3-, 4-, 5-, 6-, or 7-member ring. The carbon rings in cyclic alkyl groups can also carry alkyl groups. Cyclic alkyl groups can include bicyclic and tricyclic alkyl groups. Alkyl groups optionally include substituted alkyl groups. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cyclic alkenyl groups include those having one or more rings. Cyclic alkenyl groups include those in which a double bond is in the ring or in an alkenyl group attached to a ring. Cyclic alkenyl groups include those having a 3-, 4-, 5-, 6-, 7-, 8-, 9- or 10-member carbon ring and particularly those having a 3-, 4-, 5-, 6- or 7-member ring. The carbon rings in cyclic alkenyl groups can also carry alkyl groups. Cyclic alkenyl groups can include bicyclic and tricyclic alkyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted.

Aryl groups include groups having one or more 5- or 6-member aromatic or heteroaromatic rings. Aryl groups can contain one or more fused aromatic rings. Heteroaromatic rings can include one or more N, O, or S atoms in the ring. Heteroaromatic rings can include those with one, two or three N, those with one or two O, and those with one or two S. Aryl groups are optionally substituted. Substituted aryl groups include among others those which are substituted with alkyl or alkenyl groups, which groups in turn can be optionally substituted. Specific aryl groups include phenyl groups, biphenyl groups, pyridinyl groups, and naphthyl groups, all of which are optionally substituted.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups.

Alkylaryl groups are aryl groups substituted with one or more alkyl groups wherein the alkyl groups optionally carry additional substituents and the aryl groups are optionally substituted. Specific alkylaryl groups are alkyl-substituted phenyl groups such as methylphenyl.

The rings that may be formed from two or more of $R^1$-$R^5$ together can be optionally substituted cycloalkyl groups, optionally substituted cycloalkenyl groups or aromatic groups. The rings may contain 3, 4, 5, 6, 7 or more carbons. The rings may be heteroaromatic in which one, two or three carbons in the aromatic ring are replaced with N, O or S. The rings may be heteroalkyl or heteroalkenyl, in which one or more $CH_2$ groups in the ring are replaced with O, N, NH, or S.

Optional substitution of any alkyl, alkenyl and aryl groups includes substitution with one or more of the following substituents: halogens, —CN, —COOR, —OR, —COR, —OCOOR, —CON(R)$_2$, —OCON(R)$_2$, —N(R)$_2$, —NO$_2$, —SR, —SO$_2$R, —SO$_2$N(R)$_2$ or —SOR groups. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for alkyl, alkenyl and aryl groups include among others:

—COOR where R is a hydrogen or an alkyl group or an aryl group and more specifically where R is methyl, ethyl, propyl, butyl, or phenyl groups all of which are optionally substituted;

—COR where R is a hydrogen, or an alkyl group or an aryl groups and more specifically where R is methyl, ethyl, propyl, butyl, or phenyl groups all of which groups are optionally substituted;

—CON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;

—OCON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;

—N(R)$_2$ where each R, independently of each other R, is a hydrogen, or an alkyl group, acyl group or an aryl group and more specifically where R is methyl, ethyl, propyl, butyl, or phenyl or acetyl groups all of which are optionally substituted; or R and R can form a ring which may contain one or more double bonds.

—SR, —SO$_2$R, or —SOR where R is an alkyl group or an aryl groups and more specifically where R is methyl, ethyl, propyl, butyl, phenyl groups all of which are optionally substituted; for —SR, R can be hydrogen;

—OCOOR where R is an alkyl group or an aryl groups;

—SO$_2$N(R)$_2$ where R is a hydrogen, an alkyl group, or an aryl group and R and R can form a ring;

—OR where R═H, alkyl, aryl, or acyl; for example, R can be an acyl yielding —OCOR* where R* is a hydrogen or an alkyl group or an aryl group and more specifically where R* is methyl, ethyl, propyl, butyl, or phenyl groups all of which groups are optionally substituted;

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

Pharmaceutically acceptable salts comprise pharmaceutically-acceptable anions and/or cations. Pharmaceutically-acceptable cations include among others, alkali metal cations (e.g., $Li^+$, $Na^+$, $K^+$), alkaline earth metal cations (e.g., $Ca^{2+}$, $Mg^{2+}$), non-toxic heavy metal cations and ammonium ($NH_4^+$) and substituted ammonium ($N(R')_4^+$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., $Cl^-$, $Br^-$), sulfate, acetates (e.g., acetate, trifluoroacetate), ascorbates, aspartates, benzoates, citrates, and lactate.

Compounds of the invention can have prodrug forms. Prodrugs of the compounds of the invention are useful in the methods of this invention. Any compound that will be converted in vivo to provide a biologically, pharmaceutically or therapeutically active form of a compound of the invention is a prodrug. Various examples and forms of prodrugs are well known in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p.1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392).

The invention provides compounds having the formula CA1:

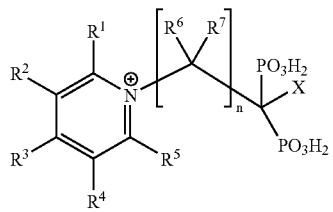

(see also FIG. 9)
or a pharmaceutically acceptable salt, ester or hydrate thereof; wherein:

X is H, —OH, or a halogen;

n is 1, 2, or 3;

$R^1$-$R^5$, independently of one another and other R groups, are selected from the group consisting of a hydrogen, a halogen, a —CN, —OR, —COOR, , —OCOOR, —COR, —CON(R)$_2$, —OCON(R)$_2$, —N(R)$_2$, —NO$_2$, —SR, —SO$_2$R, —SO$_2$N(R)$_2$ or —SOR group, an optionally substituted alkyl group, an optionally substituted alkenyl group, and an optionally substituted aryl group, where each R, independent of any other R in any listed group, is selected from H, an optionally substituted alkyl group, an optionally substituted aryl group, and an optionally substituted acyl group;

two or more of $R^1$-$R^5$ can together form one or more rings which may contain one or more double bonds or which may be aromatic;

$R^6$ and $R^7$, independently of each other and other $R^6$ and $R^7$ in the compound, are selected from the group consisting of a hydrogen, a halogen, a —N(R)$_2$, or —SR group, an optionally substituted alkyl group, an optionally substituted alkenyl group, an optionally substituted alkoxy group, and an optionally substituted aryl group, where each R, independent of any other R in any listed group, is selected from H, an optionally substituted alkyl group and an optionally substituted aryl group; and wherein $R^6$ and $R^7$ can together form a ring which may contain one or more double bonds.

In specific embodiments, the invention relates to compounds having the above formula where X is OH.

In other specific embodiments, the invention relates to compounds having the above formula where X is H.

In other specific embodiments, compounds of the invention are those of formula CA1, with the exception of the compound of formula CA1 where X is H, n is 1 and all of $R^1$-$R^7$ are hydrogens.

In other specific embodiments, the invention relates to compounds having the above formula wherein n is 1.

In other specific embodiments, the invention relates to compounds having the above formula where X is OH and n is 1.

In other specific embodiments, the invention relates to compounds having the above formula wherein one or both of $R^6$ and $R^7$ are hydrogens.

In other specific embodiments, the invention relates to compounds having the above formula wherein both of $R^6$ and $R^7$ are hydrogens.

In other specific embodiments, the invention relates to compounds having the above formula wherein both of $R^6$ and $R^7$ are hydrogens and n is 1.

In other specific embodiments, the invention relates to compounds having the above formula wherein both of $R^6$ and $R^7$ are hydrogens, n is 1 and X is OH.

In other specific embodiments, the invention relates to compounds having the above formula wherein both of $R^6$ and $R^7$ are hydrogens, n is 1 and X is H.

In other specific embodiments, the invention relates to compounds having the above formula wherein $R^1$-$R^5$ are all hydrogens.

In other specific embodiments, the invention relates to compounds having the above formula wherein $R^1$-$R^5$ are all hydrogens, X is OH and n is 1.

In other specific embodiments, the invention relates to compounds having the above formula wherein $R^1$-$R^5$ are all hydrogens, X is H and n is 1.

In other specific embodiments, the invention relates to compounds having the above formula wherein $R^1$ and $R^5$ are both hydrogens.

In other specific embodiments, the invention relates to compounds having the above formula wherein $R^1$ and $R^5$ are both hydrogen, X is OH and n is 1.

In other specific embodiments, the invention relates to compounds having the above formula wherein $R^1$ and $R^5$ are both hydrogen, X is H and n is 1.

In other specific embodiments, the invention relates to compounds having the above formula wherein $R^1$ and $R^5$ are both hydrogen and one or more of $R^2$, $R^3$ or $R^4$ is a halogen.

In other specific embodiments, the invention relates to compounds having the above formula wherein $R^1$ and $R^5$ are both hydrogens, one or more of $R^2$, $R^3$ or $R^4$ is a halogen, X is OH and n is 1.

In other specific embodiments, the invention relates to compounds having the above formula wherein $R^1$ and $R^5$ are both hydrogens, one or more of $R^2$, $R^3$ or $R^4$ is a halogen, X is H and n is 1.

In other specific embodiments, the invention relates to compounds having the above formula wherein $R^1$ and $R^5$ are both hydrogens, and one or more of $R^2$, $R^3$ or $R^4$ is an optionally substituted alkyl group, particularly a small alkyl group and more particularly a methyl group.

In other specific embodiments, the invention relates to compounds having the above formula wherein $R^1$ and $R^5$ are both hydrogens, one or more of $R^2$, $R^3$ or $R^4$ is an optionally substituted alkyl group, particularly a small alkyl group, X is OH and n is 1. Specific compounds of this invention are those as above in which $R^1$ and $R^5$ are both hydrogens, one or more of $R^2$, $R^3$ or $R^4$ is a methyl group, X is OH and n is 1. Specific compounds of this invention are those as above in which $R^1$ and $R^5$ are both hydrogens, one or more of $R^2$, $R^3$ or $R^4$ is a trifluoromethyl group, X is OH and n is 1.

In other specific embodiments, the invention relates to compounds having the above formula wherein $R^1$ and $R^5$ are both hydrogens, one or more of $R^2$, $R^3$ or $R^4$ is an optionally substituted alkyl group, particularly a small alkyl group, X is H and n is 1.

In other specific embodiments, the invention relates to compounds having the above formula wherein $R^1$ and $R^5$ are both hydrogens, and one or more of $R^2$, $R^3$ or $R^4$ is an optionally substituted alkoxy group. A specific alkoxy group is a methoxy group. Specific compounds of this invention are those as in the formula above in which $R^2$ or $R^3$ is a methoxy group.

In other specific embodiments, the invention relates to compounds having the above formula wherein $R^1$ and $R^5$ are both hydrogens, and one or more of $R^2$, $R^3$ or $R^4$ is an optionally substituted alkoxy group, X is OH and n is 1. Specific compounds of the invention are those as in the formula above wherein $R^1$ and $R^5$ are both hydrogens, $R^2$ or $R^3$ is a methoxy group, X is OH and n is 1.

In other specific embodiments, the invention relates to compounds having the above formula wherein $R^1$ and $R^5$ are both hydrogens, and one or more of $R^2$, $R^3$ or $R^4$ is an optionally substituted alkoxy group, X is H and n is 1.

In other specific embodiments, the invention relates to compounds having the above formula wherein $R^1$ and $R^5$ are both hydrogens, and one or more of $R^2$, $R^3$ or $R^4$ is an optionally substituted phenyl group.

In other specific embodiments, the invention relates to compounds having the above formula wherein $R^1$ and $R^5$ are both hydrogens, one or more of $R^2$, $R^3$ or $R^4$ is an optionally substituted phenyl group, X is OH and n is 1.

In other specific embodiments, the invention relates to compounds having the above formula wherein $R^1$ and $R^5$ are both hydrogens, one or more of $R^2$, $R^3$ or $R^4$ is an optionally substituted phenyl group, X is H and n is 1.

In other specific embodiments, the invention relates to compounds having the above formula wherein $R^1$ and $R^5$ are both hydrogens, and one or more of $R^2$, $R^3$ or $R^4$ is an alkyl-substituted phenyl group. Specific alkyl groups are methyl, ethyl and n-propyl groups. Specific compounds of this invention are those as above in which $R^2$ or $R^3$ is a 3- or 4-alkylphenyl group. Specific compounds of this invention are those as above in which $R^2$ or $R^3$ is a 3- or 4-methylphenyl group. Specific compounds of this invention are those as above in which $R^2$ or $R^3$ is a 3- or 4-ethylphenyl group. Specific compounds of this invention are those as above in which $R^2$ or $R^3$ is a 3- or 4-n-butylphenyl group.

In other specific embodiments, the invention relates to compounds having the above formula wherein $R^1$ and $R^5$ are both hydrogens, one or more of $R^2$, $R^3$ or $R^4$ is an alkyl-substituted phenyl group, X is OH and n is 1. Specific alkyl groups are methyl, ethyl and n-propyl groups. Specific compounds of this invention are those as above in which $R^2$ or $R^3$ is a 3- or 4-methylphenyl group, X is OH and n is 1. Specific compounds of this invention are those as above in which $R^2$ or $R^3$ is a 3- or 4-ethylphenyl group, X is OH and n is 1. Specific compounds of this invention are those as above in which $R^2$ or $R^3$ is a 3- or 4-n-propylphenyl group, X is OH and n is 1.

In other specific embodiments, the invention relates to compounds having the above formula wherein $R^1$ and $R^5$ are both hydrogens, one or more of $R^2$, $R^3$ or $R^4$ is an alkyl-substituted phenyl group, X is H and n is 1.

In other specific embodiments, the invention relates to compounds having the above formula wherein $R^1$ and $R^5$ are both hydrogens, and one or more of $R^2$, $R^3$ or $R^4$ is a halo-substituted phenyl group. Specific halogens are fluorine, chlorine and bromine. Specific compounds of this invention are those as above in which $R^2$ or $R^3$ is a 3- or 4-halophenyl group or a 3-, 4-dihalophenyl group. Specific compounds of this invention are those as above in which $R^2$ or $R^3$ is a 3- or 4-fluorophenyl group. Specific compounds of this invention are those as above in which $R^2$ or $R^3$ is a 3- or 4-chlorophenyl group. Specific compounds of this invention are those as above in which $R^2$ or $R^3$ is a 3- or 4-bromophenyl group. Specific compounds of this invention are those as above in which $R^2$ or $R^3$ is a 3-bromo- 4-fluorophenyl group or a 3-chloro-4-fluorophenyl group.

In other specific embodiments, the invention relates to compounds having the above formula wherein $R^1$ and $R^5$ are both hydrogens, one or more of $R^2$, $R^3$ or $R^4$ is a halo-substituted phenyl group, X is OH and n is 1. Specific halogens are fluorine, chlorine, and bromine. Specific compounds of this invention are those as above in which $R^2$ or $R^3$ is a 3- or 4-fluorophenyl group, X is OH and n is 1. Specific compounds of this invention are those as above in which $R^2$ or $R^3$ is a 3- or 4-chlorophenyl group, X is OH and n is 1. Specific compounds of this invention are those as above in which $R^2$ or $R^3$ is a 3- or 4-bromophenyl group, X is OH and n is 1. Specific compounds of this invention are those as above in which $R^2$ or $R^3$ is a 3-bromo- 4-fluorophenyl group or a 3-chloro-4-fluorophenyl group, X is OH and n is 1.

In other specific embodiments, the invention relates to compounds having the above formula wherein $R^1$ and $R^5$ are both hydrogens, one or more of $R^2$, $R^3$ or $R^4$ is a halo-substituted phenyl group, X is H and n is 1.

In other specific embodiments, the invention relates to compounds having the above formula wherein $R^1$ and $R^5$ are both hydrogens, and one or more of $R^2$, $R^3$ or $R^4$ is a hydroxy-substituted phenyl group which may be in the form of a phenoxy anion or salt thereof. Specific compounds of this invention are those as above in which $R^2$ or $R^3$ is a 3- or 4-hydroxyphenyl group. Specific compounds of this invention are those as above in which $R^2$ or $R^3$ is a 3- or 4-hydroxyphenyl group. Specific compounds of this invention are those in which $R^2$ or $R^3$ is a 3- or 4-oxyphenyl anion or a salt thereof. Salts of the oxyphenyl anion include $Na^+$, $K^+$, and other pharmaceutically acceptable salts containing pharmaceutically acceptable cations.

In other specific embodiments, the invention relates to compounds having the above formula wherein $R^1$ and $R^5$ are both hydrogens, one or more of $R^2$, $R^3$ or $R^4$ is a hydroxy-substituted phenyl group, which may be in the form of a phenoxy anion or salt thereof, X is OH and n is 1. Specific compounds of this invention are those as above in which $R^2$ or $R^3$ is a 3- or 4- hydroxyphenyl group, X is OH and n is 1. Specific compounds of this invention are those in which $R^2$ or $R^3$ is a 3- or 4-oxyphenyl anion or a salt thereof, X is OH, and n is 1. Salts of the oxyphenyl anion include $Na^+$, $K^+$, and other pharmaceutically acceptable salts containing pharmaceutically acceptable cations.

In other specific embodiments, the invention relates to compounds having the above formula wherein $R^1$ and $R^5$ are both hydrogens, and one or more of $R^2$, $R^3$ or $R^4$ is an alkoxy-substituted phenyl group. A specific alkoxy group is a methoxy group. Specific compounds of this invention are those as above in which $R^2$ or $R^3$ is a 3- or 4-methoxy phenyl group.

In other specific embodiments, the invention relates to compounds having the above formula wherein $R^1$ and $R^5$ are both hydrogens, one or more of $R^2$, $R^3$ or $R^4$ is an alkoxy substituted phenyl group, X is OH and n is 1. A specific alkoxy group is a methoxy group. Specific compounds of this invention are those as above in which $R^2$ or $R^3$ is a 3- or 4-methoxy phenyl group, X is OH and n is 1.

In other specific embodiments, the invention relates to compounds having the above formula wherein $R^1$ and $R^5$ are both hydrogens, and one or more of $R^2$, $R^3$ or $R^4$ is an optionally substituted arylalkyl group. A specific arylalkyl group is a phenylmethyl group, particularly the compound as above wherein $R^2$ or $R^3$ is a phenylmethyl group.

In other specific embodiments, the invention relates to compounds having the above formula wherein $R^1$ and $R^5$ are both hydrogens, one or more of $R^2$, $R^3$ or $R^4$ is an optionally substituted arylalkyl group, X is OH and n is 1. A specific compound of this invention is one in which $R^1$ and $R^5$ are both hydrogens, $R^2$ or $R^3$ is a phenylmethyl group, X is OH and n is 1.

In other specific embodiments, the invention relates to compounds having the above formula wherein $R^1$ and $R^5$ are both hydrogens, one or more of $R^2$, $R^3$ or $R^4$ is an optionally substituted arylalkyl group, X is H and n is 1.

In a particular embodiment of CA1, X is OH, n=1, and $R^1$-$R^7$ are H. In a particular embodiment of CA1, X is a halogen. In a more particular embodiment, the halogen is selected from the group consisting of Cl or F. In an embodiment of CA1, X is Cl. In an embodiment of CA1, X is F. In an embodiment of CA1, X is not H.

In other specific embodiments, the invention includes compounds of formula CA1, wherein n is 1, all of $R^1$, $R^3$-$R^7$ are hydrogens, X is OH or H and $R^2$ is selected from the group consisting of H, optionally substituted alkyl groups, optionally substituted alkoxy groups and optionally substituted phenyl groups. Of particular interest are those compounds in which the optional substitution is one or more halogens, including one or more fluorines or chlorines.

In other specific embodiments, the invention includes compounds of formula CA1, wherein n is 1, all of $R^1$, $R^3$-$R^7$ are hydrogens, X is OH and $R^2$ is selected from the group consisting of H, optionally substituted alkyl groups, optionally substituted alkoxy groups and optionally substituted phenyl groups. Of particular interest are those compounds in which the optional substitution is one or more halogens, including one or more fluorines or chlorines.

In other specific embodiments, the invention includes compounds of formula CA1, wherein n is 1, all of $R^1$, $R^3$-$R^7$ are hydrogens, X is OH or H and $R^2$ is selected from the group consisting of optionally substituted alkyl groups, optionally substituted alkoxy groups and optionally substituted phenyl groups. Of particular interest are those compounds in which the optional substitution is one or more halogens, including one or more fluorines or chlorines.

In other specific embodiments, the invention includes compounds of formula CA1, wherein n is 1, all of $R^1$, $R^3$-$R^7$ are hydrogens, X is OH and $R^2$ is selected from the group consisting of optionally substituted alkyl groups, optionally substituted alkoxy groups and optionally substituted phenyl groups. Of particular interest are those compounds in which the optional substitution is one or more halogens, including one or more fluorines or chlorines.

In other specific embodiments, the invention includes compounds of formula CA1, wherein n is 1, all of $R^1$, $R^3$-$R^7$ are hydrogens, X is OH or H and $R^2$ is selected from the group consisting of H, alkyl groups, alkoxy groups and a phenyl group.

In other specific embodiments, the invention includes compounds of formula CA1, wherein n is 1, all of $R^1$, $R^3$-$R^7$ are hydrogens, X is OH and $R^2$ is selected from the group consisting of H, alkyl groups, alkoxy groups and a phenyl group.

In other specific embodiments, the invention includes compounds of formula CA1, wherein n is 1, all of $R^1$, $R^3$-$R^7$ are hydrogens, X is OH or H and $R^2$ is selected from the group consisting of H, a methyl group, an ethyl group, propyl groups, butyl groups, a methoxy group, an ethoxy group, propyloxy groups, butyloxy groups and a phenyl group.

In other specific embodiments, the invention includes compounds of formula CA1, wherein n is 1, all of $R^1$, $R^3$-$R^7$ are hydrogens, X is OH and $R^2$ is selected from the group consisting of H, a methyl group, an ethyl group, propyl groups, butyl groups, a methoxy group, an ethoxy group, propyloxy groups, butyloxy groups and a phenyl group.

In other specific embodiments, the invention includes compounds of formula CA1, wherein n is 1, all of $R^1$, $R^3$-$R^7$ are hydrogens, X is OH or H and $R^2$ is selected from the group consisting of H, a methyl group, a methoxy group, and a phenyl group.

In other specific embodiments, the invention includes compounds of formula CA1, wherein n is 1, all of $R^1$, $R^3$-$R^7$ are hydrogens, X is OH and $R^2$ is selected from the group consisting of H, a methyl group, a methoxy group, and a phenyl group.

In a specific embodiment, compounds 278, 297, 300 and 446; and pharmaceutically acceptable salts, and esters thereof; are useful for treatment of a bone resorption clinical disorder.

In a specific embodiment, compounds 278, 297, 300, 444, 445 and 446; and pharmaceutically acceptable salts, and esters thereof; are useful in treatment of protozoan diseases, useful for treatment of a bone resorption clinical disorder, and for immunotherapy.

In a specific embodiment, compounds, the des-hydroxy (where X is H) analogs of compounds 278, 297, 300, 444, 445 and 446; and pharmaceutically acceptable salts, and esters thereof; are useful in the treatment of a bone resorption clinical disorder.

Compounds of this invention and compounds useful in the methods of this invention include those of the above formulas and pharmaceutically-acceptable salts and esters of those compounds. Salts include any salts derived from the acids of the formulas herein which acceptable for use in human or veterinary applications. The term esters refers to hydrolyzable esters of diphosphonate compounds of the formulas herein. Salts and esters of the compounds of the formulas herein are those which have the same therapeutic or pharmaceutical (human or veterinary) properties as the diphosphonate compounds of the formulas herein. Various combinations of salts are possible, with each phosphonate carrying a 2-, 1- or neutral charge. In principle there are multiple charge states possible, for example 9 charge states, for certain bisphosphonates of this invention.

In an embodiment, the invention provides a compound selected from the group consisting of 278, 297, 300, 335, 344, 359, 364, 398, 443-447, 449-452, 455-457, 459-462, 470-481, 483-485, ZZ1, 502, 511, 513, 520, 521, 523-526, 529-534, 542, 556, 577-579, 582, 583, 586, 588, 590, 591, 595, 597-605, 607, 610, 612, and 613; and for each respective said compound, a pharmaceutically acceptable salt or ester thereof.

In an embodiment, the invention provides a therapeutic composition comprising one or more compounds selected from the group consisting of 278, 297, 300, 335, 344, 359, 364, 398, 443-447, 449-452, 455-457, 459-462, 470-481, 483-485, ZZ1; and for each numbered compound a pharmaceutically acceptable salt or ester thereof; wherein the compounds are present in the composition in an amount or in a combined amount effective for obtaining the desired therapeutic benefit. The therapeutic compositions of this invention optionally further comprise a pharmaceutically acceptable carrier as known in the art.

In a specific embodiment, the invention includes compounds of the above formula CA1 where n=1, $R^1$ and $R^3$-$R^7$ are hydrogens, X=OH, and $R^2$=H, optionally substituted alkyl, optionally substituted alkoxy, and optionally substituted phenyl. In a more specific embodiment, the invention includes compounds where n=1, $R^1$ and $R^3$-$R^7$=H, X=OH, and $R^2$=H, alkyl, alkoxy, and phenyl. In a further specific embodiment, the invention includes compounds where n=1, $R^1$ and $R^3$-$R^7$=H, X=OH, and $R^2$=H, methyl, ethyl, propyl, butyl, methoxy, ethoxy, propoxy, butoxy, or phenyl.

In an embodiment, the invention provides various methods relating to the treatment of clinical disease. In an embodiment, the invention provides a method of treating a bone resorption disorder comprising administering to a patient in need a composition comprising a compound of the invention.

In an embodiment, the invention provides a method of treating a cancer disorder comprising administering to a patient in need a composition comprising a compound of the invention. In a specific embodiment, the cancer is breast cancer. In a specific embodiment, the breast cancer involves an actual or potential bone metastatic condition. In a specific embodiment, the invention provides a method of treating myeloma, lymphoma, prostate cancer, an epidermoid cancer, or orthotopic tumors.

In an embodiment, the invention provides compounds and methods for use in a combination therapy in the treatment of cancer. In a specific embodiment, a combination therapy utilizes a bisphosphonate compound of the invention and a different chemotherapeutic agent which can optionally be a distinct other bisphosphonate compound. In a particular embodiment the different chemotherapeutic agent is alendronate, zoledronate, risedronate, pamidronate, fas ligand (FasL), mevastatin, dexamethasone, paclitaxel, epirubicin, docetaxel, imatinib mesylate, tumor necrosis factor (TNF)-related apoptosis inducing ligand (TRAIL), uracil-tegafur, gemcitabine, melphalan, doxorubicin, vincristine, or R115777 farnesyl transferase inhibitor (FTI) (Zarnestra®). In a particular embodiment, the combination of the bisphosphonate compound of the invention and the different chemotherapeutic agent has a synergistic effect. In another particular embodiment the combination has an additive effect.

In an embodiment, the invention provides a method of treating an infectious disease comprising administering to a patient in need a composition comprising a compound of the invention. In a specific embodiment, the infectious disease relates to an agent selected from the group consisting of: a virus, a bacterium, a fungus, and a protozoan parasite. In a specific embodiment, the virus is a retrovirus. In a more specific embodiment, the retrovirus is human immunodeficiency virus (HIV). In an embodiment, the protozoan parasite is *Leishmania major*. In an embodiment, the protozoan parasite is selected from the group consisting of: *Leishmania, Toxoplasma, Cryptosporidium, Plasmodium,* and *Trypanosoma*. In an embodiment, the infectious disease is selected from the group consisting of leishmaniasis, toxoplasmosis, cryptosporidiosis, sleeping sickness, and malaria.

In an embodiment, the invention provides a method of immunotherapy comprising administering to a patient in need a composition comprising a compound of the invention. In a specific embodiment, the method stimulates T cells in the patient. In a more specific embodiment, the method stimulates gamma delta T cells.

In an embodiment, the invention provides a method of screening a bisphosphonate test compound for a potential therapeutic activity, comprising: providing said bisphosphonate test compound, measuring a performance attribute of said test compound in at least three assays selected from the group consisting of: a *Leishmania major* farnesyl diphosphate synthase (FPPS) assay, a *Dictyostelium discoideum* assay, a T cell activation assay, and a bone resorption assay, analyzing said performance attribute; and selecting said bisphosphonate test compound based on said attribute; thereby screening said bisphosphonate test compound. In a specific embodiment, the method further comprises providing a reference compound and comparing a performance attribute of said reference compound with said performance attribute of said test compound.

In an embodiment, the invention provides a method of synthesizing a bisphosphonate compound of the invention, for example formula CA1, comprising: syntheses as shown and described herein, e.g. in schemes, FIG. 2, etc.; and as further would be understood in the art.

In an embodiment, the invention provides a method of treating bone pain comprising administering to a patient in need a compound of the invention. In a particular embodiment, the treatment of bone pain is in the context of a bone disease. In a particular embodiment, the treatment of bone pain is in the context of a patient with a metastatic cancer. In a particular embodiment, the metastatic cancer has spread to a bone location or originated in a bone location. For example, the treatment of bone pain can be achieved in a breast cancer patient wherein a metastatic breast cancer can or has spread to a bone location.

DETAILED DESCRIPTION OF THE INVENTION

The invention may be further understood by the following non-limiting examples.

Example 1

Bisphosphonate Compounds

We report the design, synthesis and testing of a series of novel bisphosphonates. The most potent molecules have high activity and can represent useful compositions for a variety of applications such as in bone resorption disorders, parasitic diseases, immunomodulation, and cancer.

Our efforts led to the prediction of the importance of the presence of a positive charge at a relatively localized position in the bisphosphonate side chain. This can be related to the position of the positive charge expected in the pyridinium and imidazolium forms of compounds C3 and C4, shown above.

Figure 7:
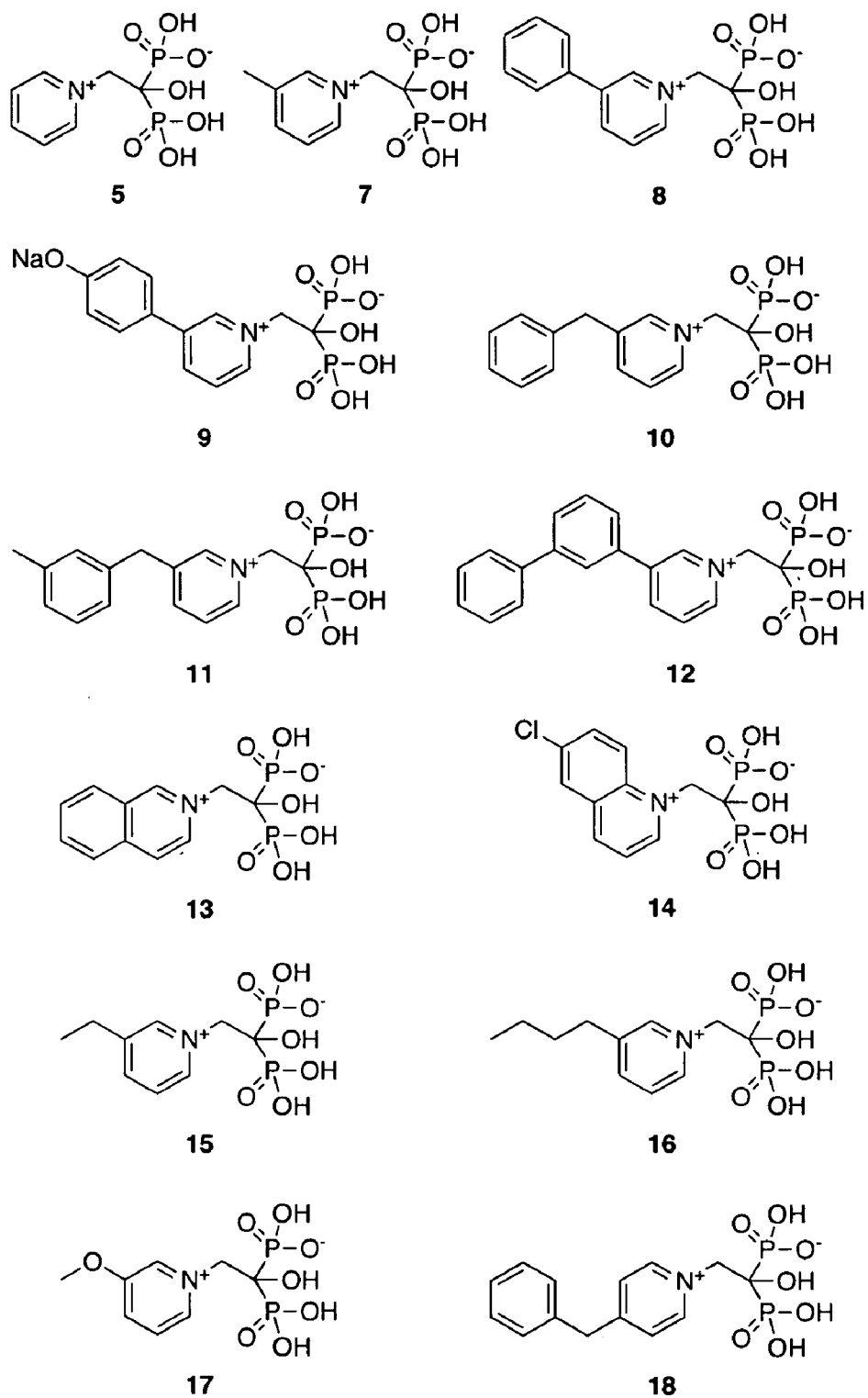
FIG. 7 illustrates the structures of pyridinium-1-yl bisphosphonates, compounds C5 and C7-C18.

We explored the possibility that the pyridinium-1-yl species, compound C5, might have useful activity. We synthesized C5 and a series of derivatives (compounds C7-C18, FIG. 7), using the following general scheme, Scheme 1.

Scheme 1:

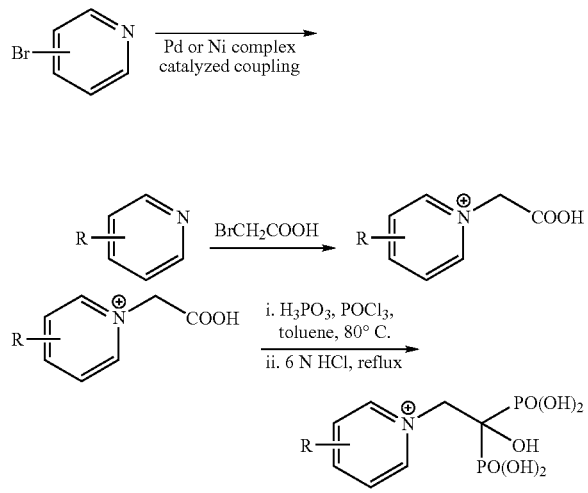

In the first step, we used (where necessary) coupling reactions of arylmetallic compounds with bromopyridines, catalyzed by Pd(PPh$_3$)$_4$ (ref. 32) or NiCl$_2$(PPh$_3$)$_2$ (ref. 33) to produce substituted pyridines. The substituted pyridines were then alkylated by using bromoacetic acid (ref. 34) and the resulting pyridinium-1-yl acetic acids were converted to the corresponding bisphosphonates by using H$_3$PO$_3$/POCl$_3$ (ref. 35).

We then investigated the activity of each compound in inhibiting the FPPS from *L. major*, in *Dictyostelium discoideum* growth inhibition and in γδ T cell activation. We used the FPPS from *L. major* since this enzyme is the putative bisphosphonate target in several trypanosomatid species. We used *D. discoideum* to test for cell growth inhibition, since this organism has been useful in the context of the development of bone resorption drugs (ref. 36). To determine the stimulatory activity of compounds C5 and C7-C18 for Vγ2Vδ2 T cells, we used the TNF-α release assay (ref. 30).

In the *L. major* FPPS inhibition assay, C5 was found to have a Ki of 18 nM (Table 6) and was thus slightly less active than the most potent commercially available bisphosphonates, zoledronate (4, Ki=11 nM in this assay) and risedronate (3, Ki=17 nM in this assay) (Table 6). In order to try to enhance activity, we next investigated the desirability of placing substituents at the meta position. We thus prepared compounds C7-C9 (FIG. 7) and tested them in the FPPS assay. The meta-methyl analog of C5 (C7) was not as active as C5 (Ki=38 nM versus 18 nM), but substitution with a meta-phenyl group, giving C8, resulted in a very potent species, having a Ki=9 nM, slightly more active than zoledronate, 4 (Ki=11 nM). The para-phenoxy derivative of C5 (C9) was found to be less active (Ki=75 nM), possibly due to unfavorable electrostatic interactions of the OH group in the FPPS active site.

TABLE 1

Activities of bisphosphonates as *L. major* FPPS inhibitors, *D. discoideum* cell growth inhibitors and gammadelta T cell simulators.*

| Compound | Compound Alias | L. major FPPS Ki (nM) | D. discoideum IC$_{50}$ (µM) | gammadelta T cell stimulation, EC$_{50}$ (µM) |
|---|---|---|---|---|
| 1 (pamidronate)[a,b] |  | 190 | 167 | 940 |
| 2 (alendronate)[a,b] |  | 95 | 32 | 52 |
| 3 (risedronate)[a,b] |  | 17 | 2.8 | 6.2 |
| 4 (zoledronate)[a,b] |  | 11 | 1.9 | 7.3 |
| 5 | 278 | 18 | 2.1 | 5.1 |
| 6 (incadronate)[a,b] |  | 23 | 1.6 | 15 |
| 7 | 297 | 38 | 1.5 | 4.6 |
| 8 | 300 | 9 | 2.8 | 3.7 |
| 9 | 359 | 75 | 2.9 | 24 |
| 10 | 335 | 160 | 8.5 | 430 |
| 11 | 344 | 70 | 9.9 | 140 |
| 12 | 364 | 950 | 2.3 | >1000 |
| 13 | 398 | 80 | 20 | 41 |
| 14 | 447 | 380 | 72 | 53 |
| 15 | 444 | 20 | 5.6 | 5.1 |
| 16 | 445 | 20 | 2.9 | 5.2 |
| 17 | 446 | 30 | 6 | 4.6 |
| 18 | 443 | 110 | 12 | 230 |

[a]*L. mayor* FPPS inhibition data from Ref. 17
[b]Gammadelta T cell stimulation data from Ref. 30
*Note that compound designations here are referred to by numbers and may optionally be designated with a preceding "C" yielding, e.g., C1, C2, etc.

Since the phenylpyridinium species, C8, displayed good activity, we next synthesized C10 and C11. Both of these compounds contain a methylene linker between the two aromatic groups and it seemed possible that they might better mimic the putative geranyl diphosphate reactive intermediate (C19):

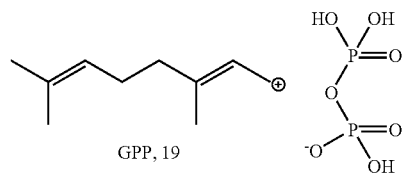

GPP, 19

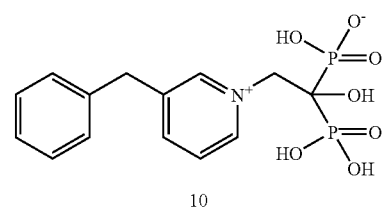

10 but each of these compounds was approximately ten-fold less active than C8, with Ki values in the 70-160 nM range, Table 1. We also prepared the biphenylpyridinium compound, C12, since the added hydrophobicity of C8 appeared encouraging, but C12 proved to be relatively inactive, having a Ki of 950 nM. The isoquinoline and quinoline species, C13 and C14, had modest activity (80 and 380 nM, respectively, for C13 and C14), but the meta- ethyl (C15), butyl (C16), methoxy (C17) and para-benzyl (C18) pyridinium species were generally more active (20, 20, 30 and 110 nM, respectively), although they were less active than compounds C3-C6, C8. See Table 1.

Figure 8:
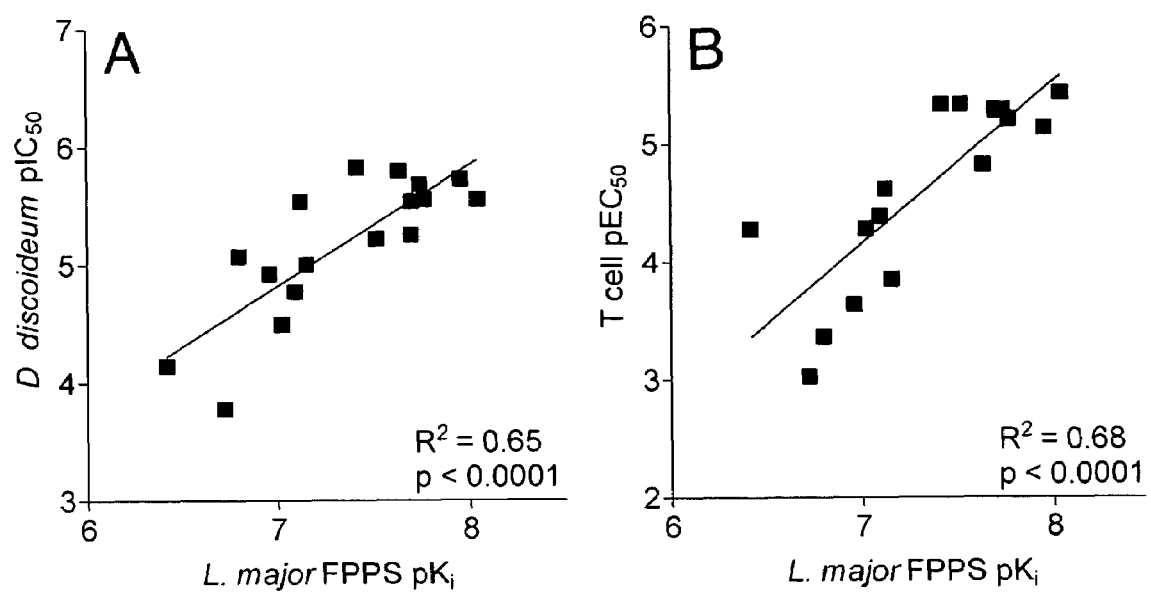
FIG. 8 illustrates correlations: A, between FPPS inhibition and *D. discoideum* growth inhibition; and B, between FPPS inhibition and γδ T cell activation (as determined by TNF-α release). The $R^2$ and p values are $R^2$=0.65 and p<0.0001 in A and $R^2$=0.68 and p<0.0001 in B.

We next investigated *D. discoideum* growth inhibition by compounds 1-18 (Table 1; alternatively referred to as C1-C18). The most active compound found was the meta- methyl pyridinium compound, C7, which had an $IC_{50}$ of 1.5 µM, followed by incadronate (C6, $IC_{50}$=1.6 µM) and zoledronate (C4, $IC_{50}$=1.9 µM). The unsubstituted pyridinium bisphosphonate, C5, was slightly more active ($IC_{50}$=2.1 µM) than was risedronate (C3, $IC_{50}$=2.8 µM). As with the FPPS inhibition results, the benzylpyridinium bisphosphonates (C10,C11,C18) were less active than the pyridinium and phenylpyridinium species (C5, C7-9). Surprisingly, C12 showed high activity, due perhaps to the possibility of an additional target in *D. discoideum* or the possibility of structural differences between *L. major* and *D. discoideum* FPPS enzymes. With the exception of C12, the activity results for the 17 bisphosphonates are highly correlated ($R^2$=0.65, $p<0.0001$), as shown in FIG. 8A.

Next, we investigated the ability of C5 and compounds C7-C18 to stimulate gammadelta T cells, using the TNF-α release assay (ref. 30). The most active compound was found to be C8 ($EC_{50}$=3.7 µM), followed by C7 and C17 ($EC_{50}$=4.6 µM), with these compounds having more activity than risedronate (C3, $EC_{50}$=6.2 µM) (ref. 30) or zoledronate (C4, $EC_{50}$=7.3 µM) (ref. 30) in this TNF-α release assay. Addition of the para hydroxyl group (8→9) again reduced activity (Table 1), and again all three methylene bridged compounds (C10,C11,C18) had poor activity. The activity results for FPPS inhibition were found to be highly correlated with gammadelta T cell TNF-α release results ($R^2$=0.68, $p<0.0001$), as shown in FIG. 8B, suggesting the likely importance of FPPS inhibition in gammadelta T cell activation (refs. 29,30).

We also explored the idea that electron withdrawing substituents on the ring could improve activity in bone resorption. To test this, compound 461 was prepared and tested, and indeed this species was found to be very potent in bone resorption. See Table 4.

Without wishing to be bound by a particular theory, these results may confirm the importance of a positive charge at the N-1 position. This suggests that the further development of this class of compounds can continue to be of interest in the context of the chemotherapy of infectious diseases, bone resorption, cancer, bone pain, and in immunotherapy.

Example 2

Structures of Bisphosphonate Compounds

Figure 1:
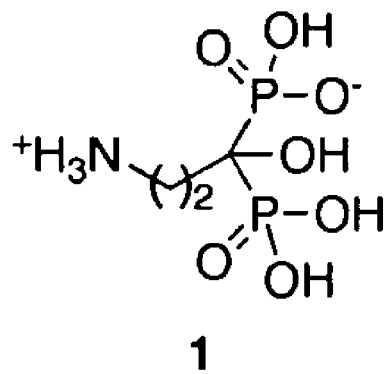
FIG. 1 illustrates compounds C1-C6, including pamidronate (Aredia®) C1; alendronate (Fosamax®) C2; risedronate (Actonel®) C3; zoledronate (Zometa®) C4; C5; and C6 shown in their zwitterionic forms.
Figure 1:
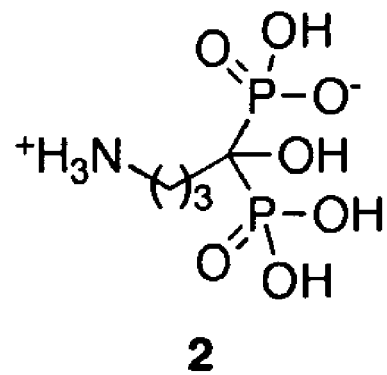
Figure 1:
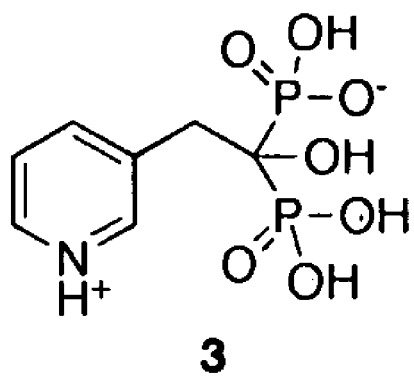
Figure 1:
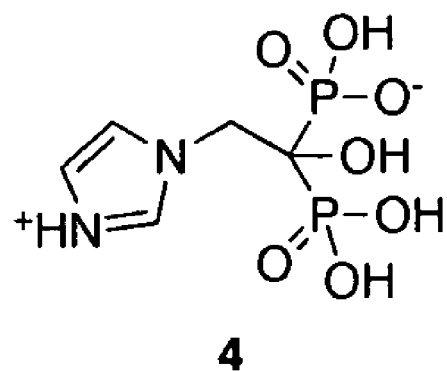
Figure 1:
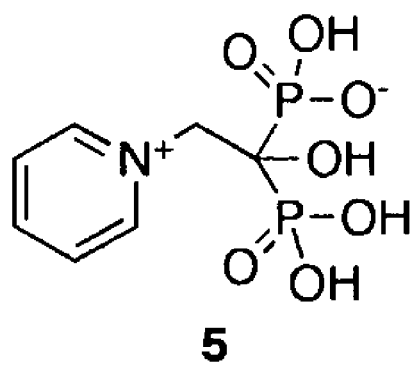
Figure 1:
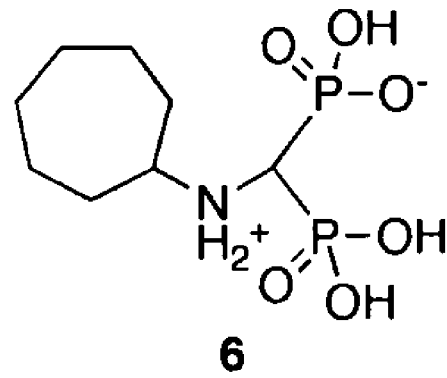
Figure 2:
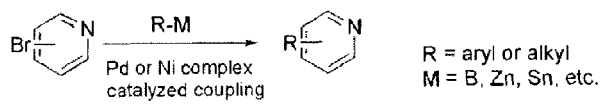
FIG. 2 illustrates synthetic routes in the preparation of compounds.
Figure 2:
Figure 2:
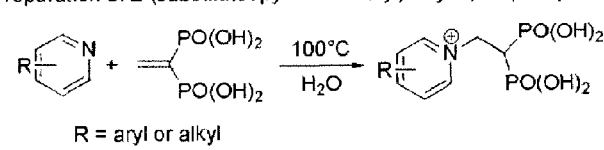
Figure 2:
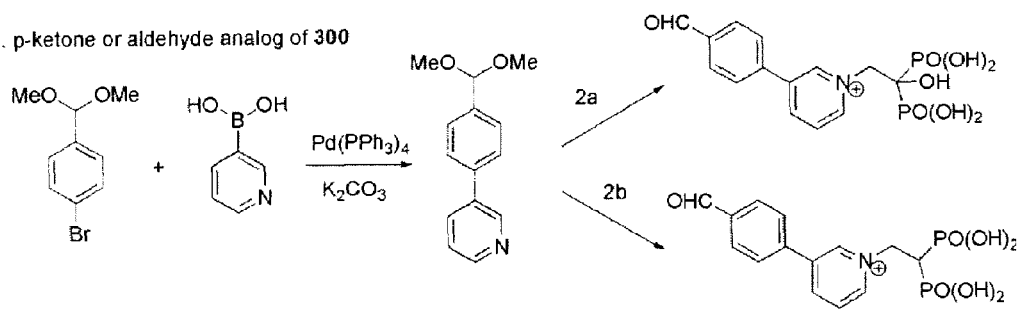
Figure 3:
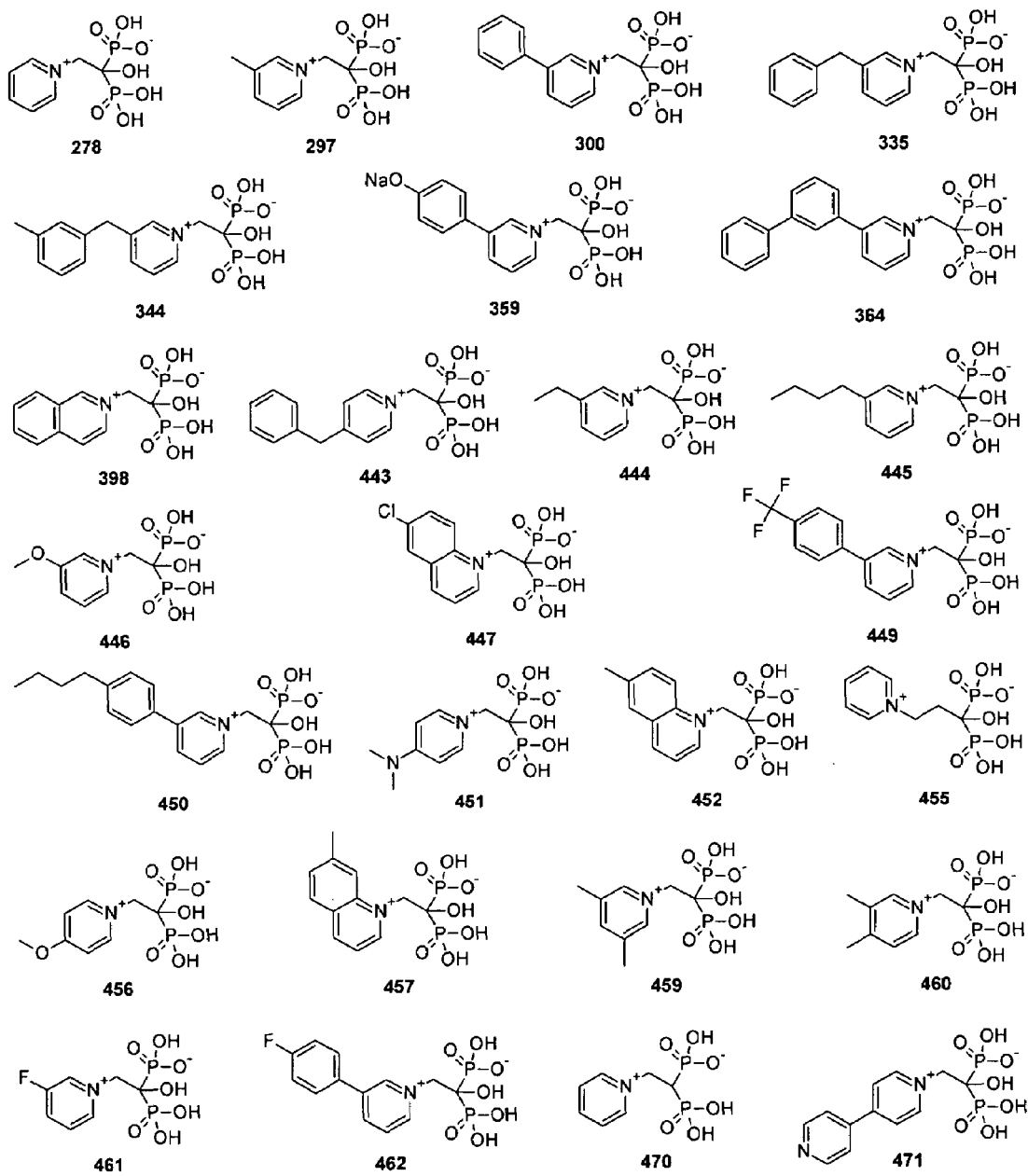
FIG. 3 illustrates structures of compounds.
Figure 4:
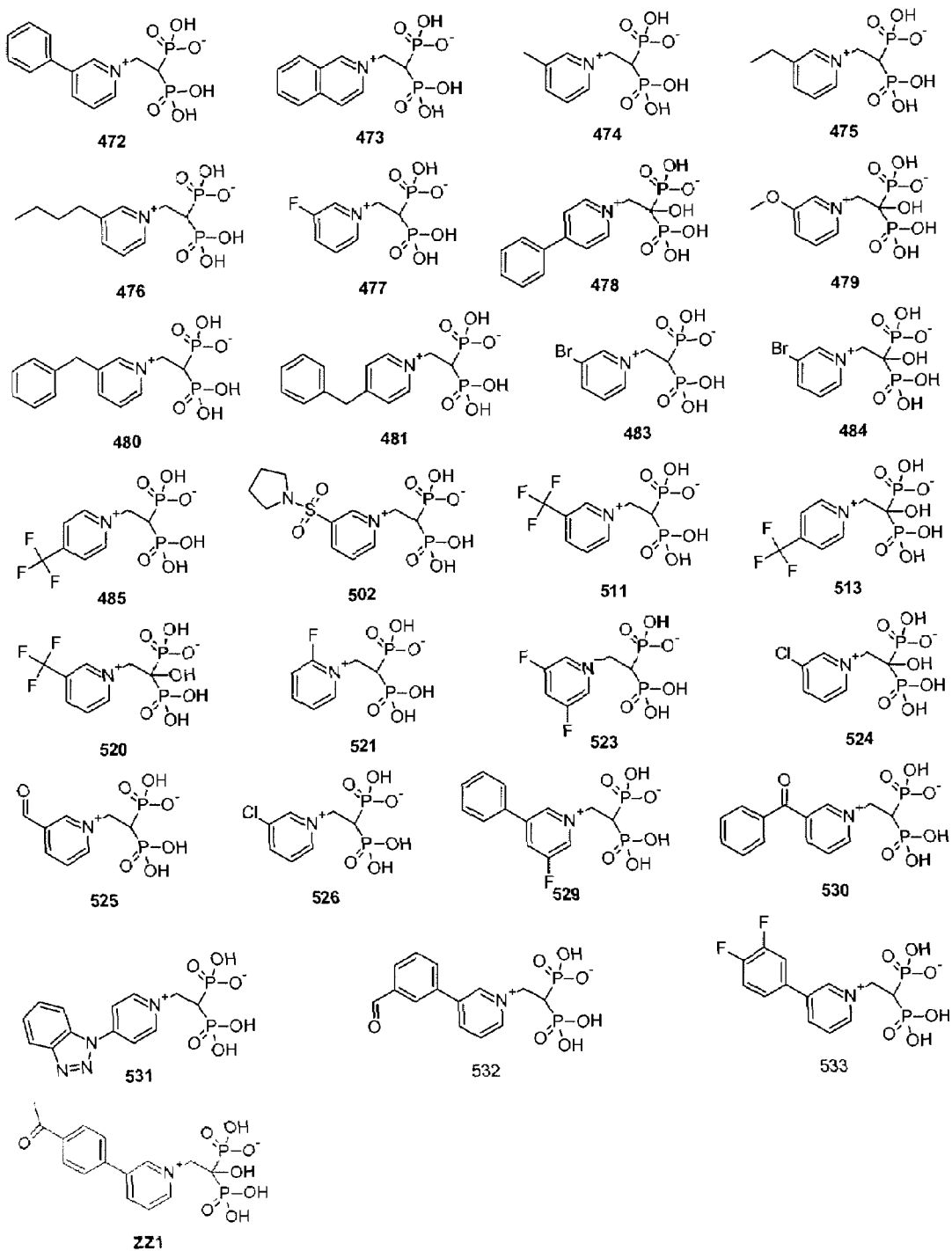
FIG. 4 illustrates structures of selected compounds.
Figure 5:
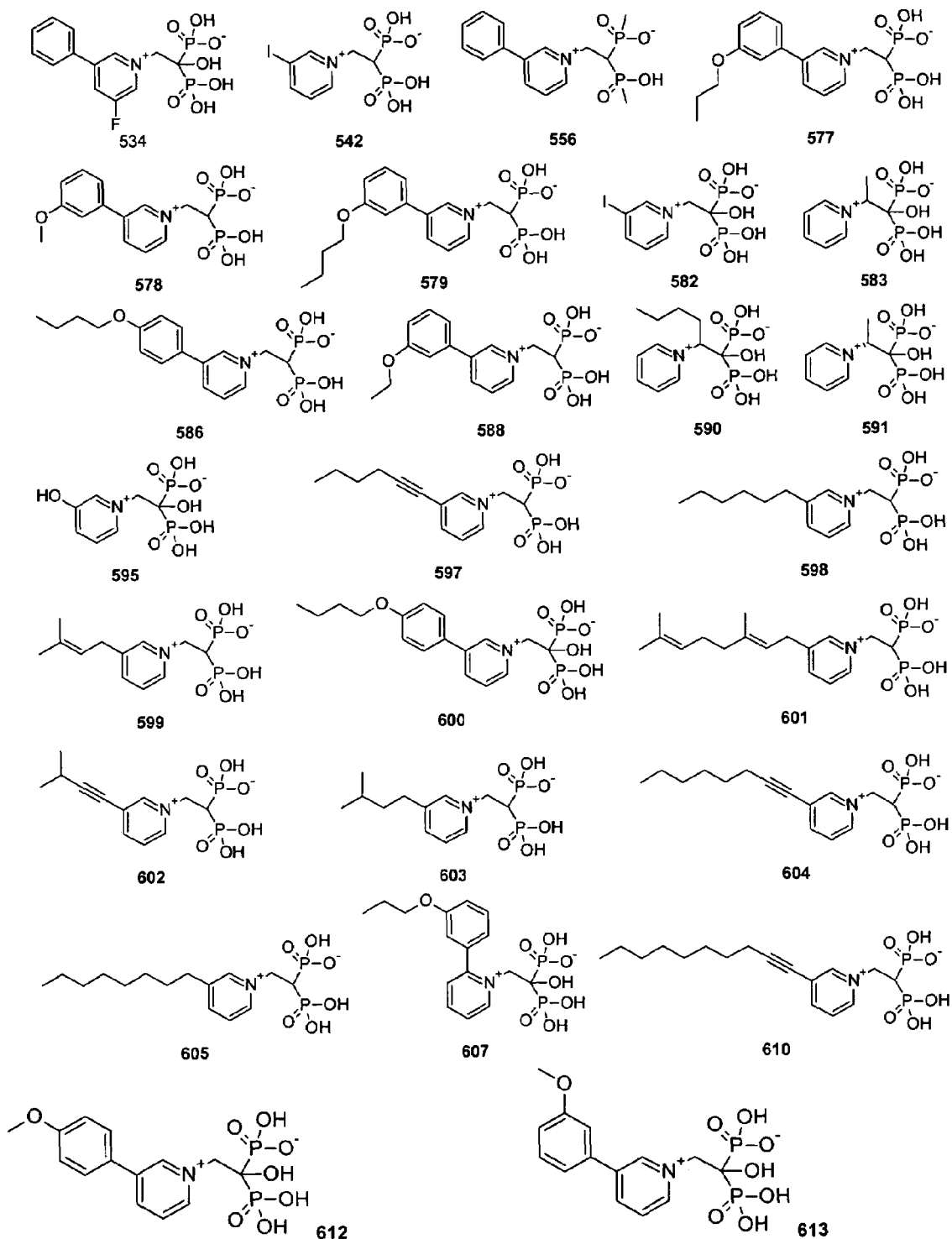
FIG. 5 illustrates structures of selected compounds.

Particular bisphosphonate compounds were synthesized. See Table 2 and the following figures: FIG. 3, FIG. 4, and FIG. 5. Note that in Table 2, the first column with the heading "Item" is not intended to refer to a compound designation, whereas the second column does refer to compound designations.

TABLE 2

Summary list of compounds with corresponding structures illustrated in FIGS. 3–5.

| Item | Compound Designation |
|---|---|
| 1 | 278 |
| 2 | 297 |
| 3 | 300 |
| 4 | 335 |
| 5 | 344 |
| 6 | 359 |
| 7 | 364 |
| 8 | 398 |
| 9 | 443 |
| 10 | 444 |
| 11 | 445 |
| 12 | 446 |
| 13 | 447 |
| 14 | 449 |
| 15 | 450 |
| 16 | 451 |
| 17 | 452 |
| 18 | 455 |
| 19 | 456 |
| 20 | 457 |
| 21 | 459 |
| 22 | 460 |
| 23 | 461 |
| 24 | 462 |
| 25 | 470 |
| 26 | 471 |
| 27 | 472 |
| 28 | 473 |
| 29 | 474 |
| 30 | 475 |
| 31 | 476 |
| 32 | 477 |
| 33 | 478 |
| 34 | 479 |
| 35 | 480 |
| 36 | 481 |
| 37 | 483 |
| 38 | 484 |
| 39 | 485 |
| 40 | ZZ1 |
| 41 | 502 |
| 42 | 511 |
| 43 | 513 |
| 44 | 520 |
| 45 | 521 |
| 46 | 523 |
| 47 | 524 |
| 48 | 525 |
| 49 | 526 |
| 50 | 529 |
| 51 | 530 |
| 52 | 531 |
| 53 | 532 |
| 54 | 533 |
| 55 | 534 |
| 56 | 542 |
| 57 | 556 |
| 58 | 577 |
| 59 | 578 |
| 60 | 579 |
| 61 | 582 |
| 62 | 583 |
| 63 | 586 |
| 64 | 588 |
| 65 | 590 |
| 66 | 591 |
| 67 | 595 |
| 68 | 597 |
| 69 | 598 |
| 70 | 599 |
| 71 | 600 |
| 72 | 601 |
| 73 | 602 |

TABLE 2-continued

Summary list of compounds with corresponding
structures illustrated in FIGS. 3–5.

| Item | Compound Designation |
|---|---|
| 74 | 603 |
| 75 | 604 |
| 76 | 605 |
| 77 | 607 |
| 78 | 610 |
| 79 | 612 |
| 80 | 613 |

Example 3

Activity of Bisphosphonate Compounds in T Cell Stimulation an Applications in Immunotherapy Additional compounds were tested for the ability to stimulate gammadelta T cells. Results are shown in Table 3.

TABLE 3 gammadelta T cell stimulation results
for selected bisphosphonate compounds.

| Compound | EC$_{50}$ (µM) |
|---|---|
| 2 | 4.7 |
| 2 | 3.5 |
| 278 | 4.8 |
| 297 | 4.9 |
| 300 | 2.1 |
| 335 | 63.4 |
| 398 | 40.6 |
| 442 | 27.5 |
| 443 | 186.6 |
| 444 | 2.8 |
| 445 | 2.5 |
| 461 | 2.7 |
| 470 | 3.3 |
| 472 | 2.1 |
| 473 | 20.1 |
| 474 | 2.4 |
| 475 | 2.8 |
| 476 | 2.0 |
| 477 | 1.8 |
| 480 | 68.7 |
| 481 | 83.4 |
| 482 | 12.5 |
| 483 | 2.9 |
| 484 | 4.6 |

Example 4

Figure 6:
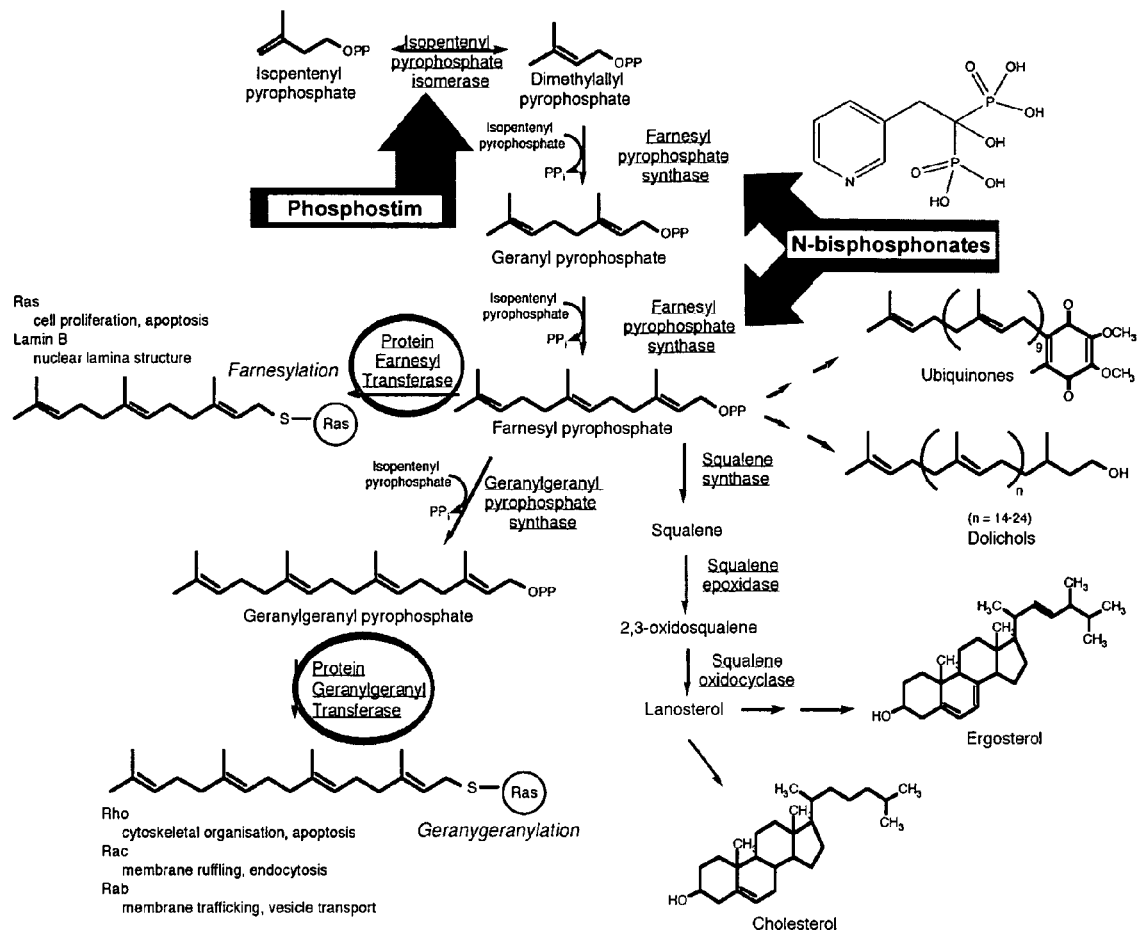
FIG. 6 illustrates cellular pathways of isoprenoid biosynthesis.

Exploration of Activity of Bisphosphonate Compounds and Strategic Design of Compounds We explored the hypothether analogs of pyrophosphate could block pyrophosphase enzymes and/or inhibit cellular growth or function. We used certain bisphosphonate compounds that are currently applied in bone resorption therapy. The compounds included pamidronate (Aredia®, Novartis), alendronate (Fosamax®, Merck), and risedronate (Actonel®, Procter & Gamble). The compounds did not appear necessarily to inhibit pyrophosphatases but did inhibit parasite cell growth. Without wishing to be bound by a particular theory, the compounds appeared to act as inhibitors of isoprenoid biosynthesis (FIG. 6).

The FPP synthase inhibitor pamidronate was observed to be effective in treating cutaneous leishmaniasis in mice. The average lesion size in treated mice was reduced during a time period of several weeks and in a dose-dependent manner relative to treated mice.

In an embodiment, a compound of the invention inhibits deoxyxylulose-5-phosphate reductoisomerase (DXR), an enzyme involved in isoprenoid biosynthesis. In a particular embodiment, a compound is able to affect *Plasmodium* in vitro or in vivo.

In an embodiment of the invention, a compound inhibits the mevalonate pathway. In an embodiment of the invention, a compound interacts with IPP isomerase (next to FPP synthase in the isoprene biosynthesis pathway) and activates gammadelta T cells.

Example 5

Activity of Bisphosphonate Compounds in Bone Resorption

Compounds are tested in a bone resorption assay: $^{45}$Ca$^{2+}$ release from 17-day old fetal mouse metatarsals (ref. 37). Results of IC$_{50}$ values for test compounds are observed and optionally compared to those for reference compounds such as risedronate (C3), alendronate (C2), and pamidronate (C1) and/or other bisphosphonate compounds known in the art. In a preferred embodiment, bisphosphonates of the invention such as the pyridinium-1-yl bisphosphonates are comparable to or more active in the bone resorption assay or in treatment of a bone resorption clinical disorder than one or more other reference bisphosphonates.

Example 6

Application of Bisphosphonate Compounds in the Treatment of Cancer

Compounds are tested for efficacy in reducing the occurrence, severity, or course of bone metastases in stage II/III breast cancer patients. A compound of the invention is found effective and administered to a patient in need of treatment. Treatment with a compound of the invention is effective in reducing the risk of bone metastasis and/or increasing the likelihood of survival, optionally in relation to treatment with a placebo. A compound is effective in enhancing a survival outcome in patients with more advanced disease. A compound administered to a cancer patient can simultaneously provide a benefit in the treatment of osteolysis and/or hypercalcemia while assisting in the prevention of bone metastasis and significantly increasing overall survival in breast cancer patients.

Compositions of the invention are applied in the treatment of skin metastases and mediastinal lymphomas. See Wilhelm et al., 2003.

Compositions of the invention are useful in the treatment of cancers such as lymphoma and myeloma and/or other forms of cancer. See Green J R, 2004, *The Oncologist* 9(supp 4):3-13; Forsea A-M et al., 2004, *British Journal of Cancer* 91:803-810.

Compositions of the invention are used in a combination therapy in the treatment of cancer. In a specific embodiment, a combination therapy utilizes a bisphosphonate compound of the invention and a different chemotherapeutic agent which can optionally be a distinct other bisphosphonate compound. See Caraglia M et al., 2004, *Oncogene* 23:6900-6913. See Salomo M et al., 2003, *British Journal of Haematology* 122:202-210.

Example 7

Application of Bisphosphonate Compounds in the Treatment of HIV Infection and AIDS Many HIV drugs are suboptimally effective in partial relation to mutations of HIV-1 reverse transcriptase that confer resistance to a drug. For example, the effectiveness of azidothymidine (AZT; zidovudine, Retrovir), is believed to be so diminished. Bisphosphonate compounds of the invention are used in conjunction with AZT to provide an improved composition and therapy. Without wishing to be bound by a particular theory, a bisphosphonate compound inhibits AZT excision caused by ATP or PPi; the inhibition results in increased AZT activity in enzyme and cellular assays. A reversion of resistance phenotype is achieved by rendering an HIV-1 strain more sensitive to AZT activity.

Example 8

Additional Bisphosphonate Compounds

Figure 9:
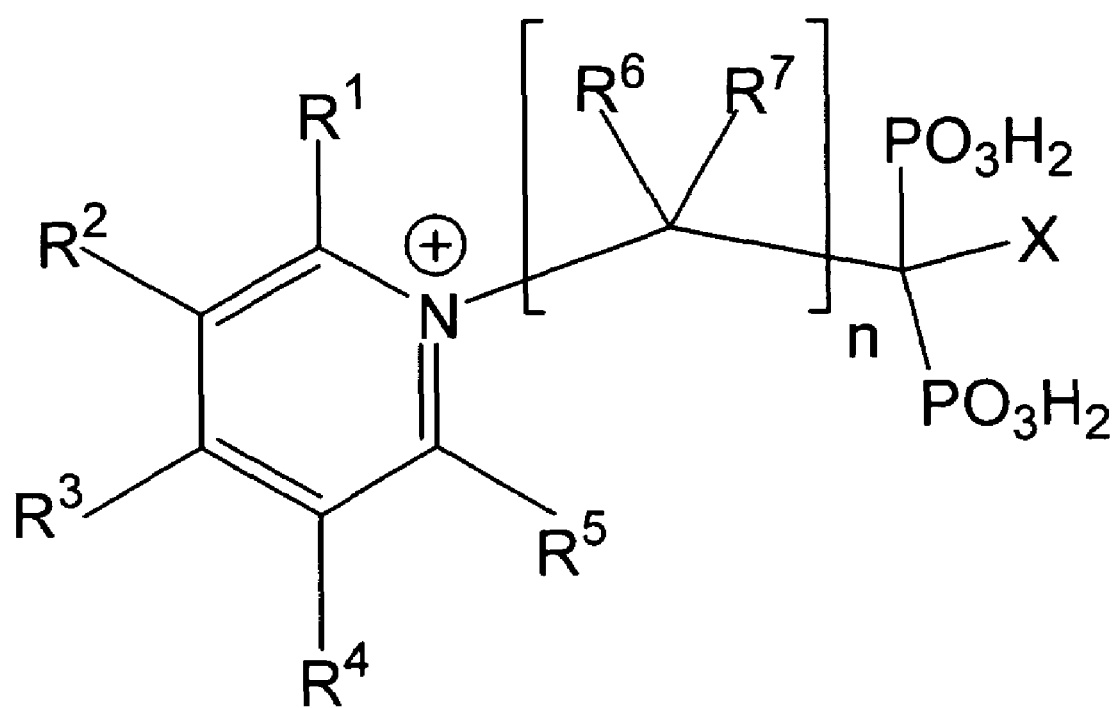
FIG. 9 illustrates a structure of a bisphosphonate compound.

Further bisphosphonate compounds were synthesized. The structures are indicated in FIG. 9, FIG. 10, and FIG. 11. As noted in other Examples herein, the functional activity of certain of these compounds was assessed.

Example 9

Bisphosphonate Compounds have Activity in Several Contexts Relating to Bone Resorption and Immune Regulation We have obtained data for selected bisphosphonate compounds in the contexts of *D. discoideum* assays, human FPPS assays, gammadelta T cell stimulation assays, and bone resorption assays. Several compounds showed substantial activity in one or more functional assays. Some toxicity testing was also performed. See Table 4 (in some instances, the same data depicted elsewhere herein, e.g., in Table 1, may be presented again to facilitate comparative analysis).

TABLE 4

| Compound | (1) *D. discoideum* $IC_{50}$ (uM) | (2) human FPPS $IC_{50}$ (uM) | (3) gammadelta T cell stimulation $EC_{50}$ | (4) Bone resorption $IC_{50}$ (uM) | (5) Toxicity $IC_{50}$ (ug/mL - human nasopharyngeal carcinoma cells) |
|---|---|---|---|---|---|
| 278 | 2.6 | 1.6 | 5.1 | 0.67 | 300 |
| 297 | 2.8 | NT | 4.6 | 0.22 | 5.3 |
| 300 | 2.8 | 1.7 | 3.7 | 0.41 | 5.4 |
| 335 | 11 | NT | 430 | NT | NT |
| 344 | 8.5 | 17 | 140 | NT | NT |
| 359 | 2.9 | NT | 24 | NT | NT |
| 364 | 2.3 | 37 | >1000 | NT | NT |
| 398 | 20 | NT | 41 | NT | NT |
| 443 | 12 | NT | 230 | NT | NT |
| 444 | 5.6 | NT | 5.1 | NT | NT |
| 445 | 3 | NT | 5.2 | NT | NT |
| 446 | 6 | NT | 4.6 | 0.37 | NT |
| 447 | 72 | NT | 53 | NT | NT |
| 449 | 4 | NT | 12 | NT | NT |
| 450 | 4.2 | NT | 6.8 | NT | NT |
| 451 | 31 | 280 | inactive | NT | NT |
| 452 | 73 | NT | 250 | NT | NT |
| 455 | 27 | NT | 25 | NT | NT |
| 456 | 27 | NT | 19 | NT | NT |
| 457 | 14 | NT | 1900 | NT | NT |
| 459 | 27 | NT | 14 | NT | NT |
| 460 | 14 | NT | 13 | NT | NT |
| 461 | 3.7 | NT | 2.7 | 0.075 | NT |
| 462 | 2.7 | NT | 15 | NT | NT |
| 470 | 3.5 | NT | NT | NT | NT |
| 471 | inactive | NT | inactive | NT | NT |
| 472 | 2.5 | NT | NT | NT | NT |
| 473 | 20 | NT | NT | NT | NT |
| 474 | 4.4 | NT | NT | NT | NT |
| 475 | 4.1 | NT | NT | NT | NT |
| 476 | 2.3 | NT | NT | NT | NT |
| 477 | 2.7 | 1.4 | NT | NT | NT |
| 478 | 760 | NT | inactive | NT | NT |
| 479 | 6 | NT | 15 | NT | NT |
| 480 | 3 | NT | NT | NT | NT |
| 481 | 3.5 | NT | NT | NT | NT |
| 483 | 2.5 | NT | NT | NT | NT |
| 484 | 3.5 | 2.5 | NT | NT | NT |
| 485 | 58 | NT | 370 | NT | NT |
| 502 | 100 | NT | inactive | NT | NT |
| 511 | 4.1 | 2.5 | 14 | NT | NT |
| 513 | 1500 | NT | 550 | NT | NT |
| 520 | 6.3 | NT | 14 | NT | NT |
| 521 | 570 | NT | 790 | NT | NT |
| 523 | 4.6 | NT | 11 | NT | NT |

TABLE 4-continued

| Compound | (1) D. discoideum IC$_{50}$ (uM) | (2) human FPPS IC$_{50}$ (uM) | (3) gammadelta T cell stimulation EC$_{50}$ | (4) Bone resorption IC$_{50}$ (uM) | (5) Toxicity IC$_{50}$ (ug/mL - human nasopharyngeal carcinoma cells) |
|---|---|---|---|---|---|
| 524 | 2.4 | NT | 10 | NT | NT |
| 525 | 8.4 | NT | 11 | NT | NT |
| 526 | 2.1 | 1.2 | 8.6 | NT | NT |
| 529 | 3.3 | NT | 9.4 | NT | NT |
| 530 | 190 | NT | 6500 | NT | NT |
| 531 | 20 | NT | inactive | NT | NT |
| 532 | 4.1 | NT | 41 | NT | NT |
| 533 | NT | NT | 19 | NT | NT |
| 534 | no tested | NT | 16 | NT | NT |
| 542 | 1.7 | 1.2 | 12 | NT | NT |
| 556 | inactive | NT | 2300 | NT | NT |
| 577 | 4.1 | NT | 21 | NT | NT |
| 578 | 4 | NT | 20 | NT | NT |
| 579 | 6 | NT | 20 | NT | NT |
| 582 | 3.5 | 1.6 | NT | NT | NT |
| 583 | 14 | NT | 50 | NT | NT |
| 586 | 6 | NT | 90 | NT | NT |
| 588 | 3.3 | 11 | 120 | NT | NT |
| 590 | 9.1 | 23 | 300 | NT | NT |
| 591 | 38 | 29 | NT | NT | NT |
| 595 | 49 | 2.7 | 210 | NT | NT |
| 597 | 2.0 | 1.9 | 58 | NT | NT |
| 598 | 1.7 | NT | 35 | NT | NT |
| 599 | 1.7 | NT | 69 | NT | NT |
| 600 | 11 | NT | 290 | NT | NT |
| 601 | 2.4 | NT | 220 | NT | NT |
| 602 | 2.04 | NT | 18 | NT | NT |
| 603 | NT | NT | 22 | NT | NT |
| 604 | NT | NT | 10 | NT | NT |
| 605 | NT | NT | 6 | NT | NT |
| 607 | NT | NT | NT | NT | NT |
| 610 | NT | NT | NT | NT | NT |
| 612 | NT | NT | NT | NT | NT |
| 613 | NT | NT | NT | NT | NT |
| 614 | NT | NT | NT | NT | NT |
| 615 | NT | 5.2 | NT | NT | NT |

NT, not tested.

Example 10

Activity of Bisphosphonate Compounds Against *Trypanosoma* and *Leishmania* Parasites We have obtained data for selected bisphosphonate compounds against parasites including *Trypanosoma brucei*, *Trypanosoma cruzi*, and *Leishmania major*. Several compounds showed substantial activity in one or more functional assays. See Table 5 (in some instances, the same data depicted elsewhere herein, e.g., in Table 1, may be presented again to facilitate comparative analysis).

TABLE 5

| Compound | (6) T. brucei FPPS IC$_{50}$ (uM) | (7) L. major FPPS Ki (nM) | (8) T. cruzi IC$_{50}$ (ug/mL) | (9) T. brucei soluble vacuolar pyrophosphatase IC$_{50}$ (uM) |
|---|---|---|---|---|
| 278 | 0.83 | 18 | 3.07 | NT |
| 297 | NT | 38 | NT | NT |
| 300 | 0.58 | 9 | NT | 35 |
| 335 | NT | 160 | NT | 70 |
| 344 | NT | 70 | NT | 78 |
| 359 | NT | 75 | NT | NT |
| 364 | NT | 950 | NT | NT |
| 398 | NT | 80 | NT | NT |
| 443 | NT | 110 | NT | NT |
| 444 | NT | 20 | NT | NT |
| 445 | NT | 20 | NT | NT |
| 446 | NT | 30 | NT | NT |
| 447 | NT | 380 | NT | NT |
| 449 | NT | NT | NT | NT |
| 450 | NT | NT | NT | NT |
| 451 | NT | NT | NT | NT |
| 452 | NT | NT | NT | NT |
| 455 | NT | NT | NT | NT |
| 456 | NT | NT | NT | NT |
| 457 | NT | NT | NT | NT |
| 459 | NT | NT | NT | NT |
| 460 | NT | NT | NT | NT |
| 461 | 0.54 | 50 | NT | NT |
| 462 | NT | NT | NT | NT |
| 470 | 0.79 | NT | NT | NT |
| 471 | NT | NT | NT | NT |
| 472 | NT | NT | NT | NT |
| 473 | NT | NT | NT | NT |
| 474 | NT | NT | NT | NT |
| 475 | NT | NT | NT | NT |
| 476 | NT | NT | NT | NT |

TABLE 5-continued

| Compound | (6) T. brucei FPPS IC$_{50}$ (uM) | (7) L. major FPPS Ki (nM) | (8) T. cruzi IC$_{50}$ (ug/mL) | (9) T. brucei soluble vacuolar pyrophosphatase IC$_{50}$ (uM) |
|---|---|---|---|---|
| 477 | 0.89 | NT | NT | NT |
| 478 | NT | NT | NT | NT |
| 479 | NT | NT | NT | NT |
| 480 | NT | NT | NT | NT |
| 481 | NT | NT | NT | NT |
| 483 | 0.43 | NT | NT | NT |
| 484 | 1.1 | NT | NT | NT |
| 485 | NT | NT | NT | NT |
| 502 | NT | NT | NT | NT |
| 511 | 0.76 | NT | NT | NT |
| 513 | NT | NT | NT | NT |
| 520 | 0.65 | NT | NT | NT |
| 521 | NT | NT | NT | NT |
| 523 | NT | NT | NT | NT |
| 524 | 0.26 | NT | NT | NT |
| 525 | NT | NT | NT | NT |
| 526 | 0.54 | NT | NT | NT |
| 529 | NT | NT | NT | NT |
| 530 | NT | NT | NT | NT |
| 531 | NT | NT | NT | NT |
| 532 | NT | NT | NT | NT |
| 533 | NT | NT | NT | NT |
| 534 | NT | NT | NT | NT |
| 542 | 0.39 | NT | NT | NT |
| 556 | NT | NT | NT | NT |
| 577 | NT | NT | NT | NT |
| 578 | NT | NT | NT | NT |
| 579 | NT | NT | NT | NT |
| 582 | NT | NT | NT | NT |
| 583 | 4.6 | NT | NT | NT |
| 586 | NT | NT | NT | NT |
| 588 | NT | NT | NT | NT |
| 590 | NT | NT | NT | NT |
| 591 | NT | NT | NT | NT |
| 595 | NT | NT | NT | NT |
| 597 | NT | NT | NT | NT |
| 598 | 0.59 | NT | NT | NT |
| 599 | 0.54 | NT | NT | NT |
| 600 | NT | NT | NT | NT |
| 601 | 2.1 | NT | NT | NT |
| 602 | 1 | NT | NT | NT |
| 603 | 0.71 | NT | NT | NT |
| 604 | 0.57 | NT | NT | NT |
| 605 | 0.29 | NT | NT | NT |
| 607 | NT | NT | NT | NT |
| 610 | NT | NT | NT | NT |
| 612 | NT | NT | NT | NT |
| 613 | NT | NT | NT | NT |
| 614 | NT | NT | NT | NT |
| 615 | NT | NT | NT | NT |

NT, not tested.

Statements Regarding Incorporation by Reference and Variations

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

When a group of substituents is disclosed herein, it is understood that all individual members of those groups and all subgroups, including any isomers and enantiomers of the group members, and classes of compounds that can be formed using the substituents are disclosed separately. When a Markush group or other grouping is used herein, all individual members of the group and all combinations and subcombinations possible of the group are intended to be individually included in the disclosure. When a compound is described herein such that a particular isomer or enantiomer of the compound is not specified, for example, in a formula or in a chemical name, that description is intended to include each isomer and enantiomer of the compound described individually or in any combination. When an atom is described herein, including in a composition, any isotope of such atom is intended to be included. Specific names of compounds are intended to be exemplary, as it is known that one of ordinary skill in the art can name the same compounds differently. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

Where the terms "comprise", "comprises", "comprised", or "comprising" are used herein, they are to be interpreted as specifying the presence of the stated features, integers, steps, or components referred to, but not to preclude the presence or addition of one or more other feature, integer, step, component, or group thereof.

The invention has been described with reference to various specific and preferred embodiments and techniques. However, it should be understood that many variations and modifications may be made while remaining within the spirit and scope of the invention. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques described herein are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example or illustration and not of limitation.

REFERENCES (1) Sambrook, P. N.; Geusens, P.; Ribot, C.; Solimano, J. A.; Ferrer-Barriendos, J.; Gaines, K.; Verbruggen, N.; Melton, M. E. Alendronate produces greater effects than raloxifene on bone density and bone turnover in postmenopausal women with low bone density: results of EFFECT (EFficacy of FOSAMAX versus EVISTA Comparison Trial) International. J. Intern. Med. 2004, 255, 503-511.

(2) Vasireddy, S.; Talwakar, A.; Miller, H.; Mehan, R.; Swinson, D. R. Patterns of pain in Paget's disease of bone and their outcomes on treatment with pamidronate. Clin. Rheumatol. 2003, 22, 376-380.

(3) Dawson, N. A. Therapeutic benefit of bisphosphonates in the management of prostate cancer-related bone disease. Expert. Opin. Pharmacother. 2003, 4, 705-716.

(4) Rosen, L. S.; Gordon, D. H.; Dugan, W. Jr.; Major, P.; Eisenberg, P. D.; Provencher, L.; Kaminski, M.; Simeone, J.; Seaman, J.; Chen, B. L.; Coleman, R. E. Zoledronic acid is superior to pamidronate for the treatment of bone metastases in breast carcinoma patients with at least one osteolytic lesion. Cancer 2004, 100, 36-43.

(5) Cromartie, T. H.; Fisher, K. J.; Grossman, J. N. The discovery of a novel site of action for herbicidal bisphosphonates. Pesticide Biochem. Phys. 1999, 63, 114-126.

(6) Cromartie, T. H.; Fisher, K. J. Method of controlling plants by inhibition of farnesyl pyrophosphate synthase. U.S. Pat. No. 5,756,423, May 26, 1998.

(7) van Beek, E.; Pieterman, E.; Cohen, L.; Löwik, C.; Papapoulos, S. Nitrogen-containing bisphosphonates inhibit isopentenyl pyrophosphate isomerase/farnesyl pyrophosphate synthase activity with relative potencies corresponding to their antiresorptive potencies in vitro and in vivo. Biochem. Biophys. Res. Commun. 1999, 255, 491-494.

(8) van Beek, E.; Pieterman, E.; Cohen, L.; Löwik, C.; Papapoulos, S. Farnesyl pyrophosphate synthase is the molecular target of nitrogen-containing bisphosphonates. Biochem. Biophys. Res. Commun. 1999, 264, 108-111.

(9) Keller, R. K.; Fliesler, S. J. Mechanism of aminobisphosphonate action: characterization of alendronate inhibition of the isoprenoid pathway. Biochem. Biophys. Res. Commun. 1999, 266, 560-563.

(10) Bergstrom, J. D.; Bostedor, R. G.; Masarachia, P. J.; Reszka, A. A.; Rodan, G. Mechanism of aminobisphosphonate action: characterization of alendronate inhibition of the isoprenoid pathway. Arch. Biochem. Biophys. 2000, 373, 231-241.

(11) Grove, J. E.; Brown, R. J.; Watts, D. J. The intracellular target for the antiresorptive aminobisphosphonate drugs in *Dictyostelium discoideum* is the enzyme farnesyl diphosphate synthase. J. Bone Miner. Res. 2000, 15, 971-981.

(12) Dunford, J. E.; Thompson, K.; Coxon, F. P.; Luckman, S. P.; Hahan, F. M.; Poulter, C. D.; Ebetino, F. H.; Rogers, M. J. Structure-activity relationships for inhibition of farnesyl diphosphate synthase in vitro and inhibition of bone resorption in vivo by nitrogen-containing bisphosphonates. J. Pharmacol. Exp. Ther. 2001, 296, 235-242.

(13) Luckman, S. P.; Hughes, D. E.; Coxon, F. P.; Graham, R.; Russell, G.; Rogers, M. J. Nitrogen-containing bisphosphonates inhibit the mevalonate pathway and prevent post-translational prenylation of GTP-binding proteins, including Ras. J. Bone Miner. Res. 1998,13, 581-589.

(14) Fisher, J. E.; Rogers, M. J.; Halasy, J. M.; Luckman, S. P.; Hughes, D. E.; Masarachia, P. J.; Wesolowski, G.; Russell, R. G.; Rodan, G. A.; Reszka, A. A. Alendronate mechanism of action: geranylgeraniol, an intermediate in the mevalonate pathway, prevents inhibition of osteoclast formation, bone resorption, and kinase activation in vitro. Proc. Natl. Acad. Sci. USA 1999, 96,133-138.

(15) van Beek, E.; Löwik, C.; van der Pluijm, G.; Papapoulos, S. The role of geranylgeranylation in bone resorption and its suppression by bisphosphonates in fetal bone explants in vitro: A clue to the mechanism of action of nitrogen-containing bisphosphonates. J. Bone Miner. Res. 1999, 14, 722-729.

(16) Montalvetti, A.; Bailey, B. N.; Martin, M. B.; Severin, G. W.; Oldfield, E.; Docampo, R. Bisphosphonates are potent inhibitors of *Trypanosoma cruzi* farnesyl pyrophosphate synthase. J. Biol. Chem. 2001, 276, 33930-33937.

(17) Sanders, J. M.; Gómez, A. O.; Mao, J.; Meints, G. A.; van Brussel, E. M.; Burzynska, A.; Kafarski, P.; González-Pacanowska, D.; Oldfield, E. 3-D QSAR investigations of the inhibition of *Leishmania major* farnesyl pyrophosphate synthase by bisphosphonates. J. Med. Chem. 2003, 46, 5171-5183.

(18) Martin, M. B.; Grimley, J. S.; Lewis, J. C.; Heath, H. T. III; Bailey, B. N.; Kendrick, H.; Yardley, V.; Caldera, A.; Lira, R.; Urbina, J. A.; Moreno, S. N.; Docampo, R.; Croft, S. L.; Oldfield, E. Bisphosphonates inhibit the growth of *Trypanosoma brucei, Trypanosoma cruzi, Leishmania donovani, Toxoplasma gondii*, and *Plasmodium falciparum*: A potential route to chemotherapy. J. Med. Chem. 2001, 44, 909-916.

(19) Martin, M. B.; Sanders, J. M.; Kendrick, H.; de Luca-Fradley, K.; Lewis, J. C.; Grimley, J. S.; van Brussel, E. M.; Olsen, J. R.; Meints, G. A.; Burzynska, A.; Kafarski, P.; Croft, S. L.; Oldfield, E. Activity of bisphosphonates against *Trypanosoma brucei* rhodesiense. J. Med. Chem. 2002, 45, 2904-2914.

(20) Moreno, B.; Bailey, B. N.; Luo, S.; Martin, M. B.; Kuhlenschmidt, M.; Moreno, S. N.; Docampo, R.; Oldfield, E. 31P NMR of apicomplexans and the effects of risedronate on *Cryptosporidium parvum* growth. Biochem. Biophys. Res. Commun. 2001, 284, 632-637.

(21) Ghosh, S.; Chan, J. M.; Lea, C. R.; Meints, G. A.; Lewis, J. C.; Tovian, Z. S.; Flessner, R. M.; Loftus, T. C.; Bruchhaus, I.; Kendrick, H.; Croft, S. L.; Kemp, R. G.; Kobayashi, E. Effects of bisphosphonates on the growth of *Entamoeba histolytica* and *Plasmodium* species in vitro and in vivo. J. Med. Chem. 2004, 47, 175-187.

(22) Yardley, V.; Khan, A. A.; Martin, M. B.; Slifer, T. R.; Araujo, F. G.; Moreno, S. N.; Docampo, R.; Croft, S. L.; Oldfield, E. In vivo activities of farnesyl pyrophosphate synthase inhibitors against *Leishmania donovani* and *Toxoplasma gondii*. Antimicrob. Agents Chemother. 2002, 46, 929-931.

(23) Rodriguez, N.; Bailey, B. N.; Martin, M. B.; Oldfield, E.; Urbina, J. A.; Docampo, R. Radical cure of experimental cutaneous leishmaniasis by the bisphosphonate pamidronate. J. Infect. Dis. 2002, 186,138-140.

(24) Garzoni, L. R.; Caldera, A.; Meirelles, M. N. L.; de Castro, S. L.; Meints, G.; Docampo, R.; Oldfield, E.; Urbina, J. A. Selective in vitro effects of the farnesyl pyrophosphate synthase inhibitor risedronate on *Trypanosoma cruzi*. Intl. J. Antimicrobial Agents 2004, 23, 273-285.

(25) Garzoni, L. R.; Waghabi, M. C.; Baptista, M. M.; de Castro, S. L.; Meirelles, M. N. L.; Britto, C.; Docampo, R.; Oldfield, E.; Urbina, J. A. Antiparasitic activity of risedronate in a murine model of acute Chagas' disease. Intl. J. Antimicrobial Agents 2004, 23, 286-290.

(26) Wang, L.; Kamath, A.; Das, H.; Li, L.; Bukowski, J. F. Antibacterial effect of human Vgamma2Vdelta2 T cells in vivo. J. Clin. Invest. 2001, 108, 1349-1357.

(27) Kunzmann, V.; Bauer, E.; Feurle, J.; Weissinger, F.; Tony, H. P.; Wilhelm, M. Stimulation of γδ T cells by aminobisphosphonates and induction of antiplasma cell activity in multiple myeloma. Blood 2000, 96, 384-392.

(28) Kato, Y.; Tanaka, Y.; Miyagawa, F.; Yamashita, S.; Minato, N. Targeting of tumor cells for human gammadelta T cells by nonpeptide antigens. J. Immunol. 2001, 167, 5092-5098.

(29) Thompson, K.; Rogers, M. J. Statins prevent bisphosphonate-induced gammadelta-T-cell proliferation and activation in vitro. J. Bone Miner. Res. 2004, 19, 278-288.

(30) Sanders, J. M.; Ghosh, S.; Chan, J. M. W.; Meints, G.; Wang, H.; Raker, A. M.; Song, Y.; Colantino, A.; Burzynska, A.; Kafarski, P.; Morita, C. T.; Oldfield, E. Quantitative structure-activity relationships for gammadelta T cell activation by bisphosphonates. J. Med. Chem. 2004, 47, 375-384.

(31) Wilhelm, M.; Kunzmann, V.; Eckstein, S.; Reimer, P.; Weissinger, F.; Ruediger, T.; Tony, H. P. gammadelta T cells for immune therapy of patients with lymphoid malignancies. Blood 2003, 102, 200-206.

(32) Miyaura, N; Yanagi, T; Suzuki, A. The palladium-catalyzed cross-coupling reaction of phenylboronic acid with haloarenes in the presence of bases. Synth. Commun. 1981, 11, 513-519.

(33) Krapcho, A. P.; Ellis, M. Synthesis of regioisomeric difluoro- and 8-chloro-9-fluorobenz[g]isoquinoline-5,10-diones and SNAr displacements studies by diamines: bis (aminoalkyl)aminobenz[g]isoquinoline-5,10-diones. J. Fluorine Chem. 1998, 90, 139-147.

(34) Zhang, L.; Liang, F.; Sun, L.; Hu, Y.; Hu, H. A novel and practical synthesis of 3-unsubstituted indolizines. Synthesis 2000, 1733-1737.

(35) Harel, Z.; Kovalevski-Liron, E.; Lidor-Hadas, R.; Lifshitz-Liron, R. Use of certain diluents for making bisphosphonic acids. World Patent WO03097655, Nov. 27, 2003.

(36) Rogers, M. J.; Watts, D. J.; Russell, R. G.; Ji, X.; Xiong, X.; Blackburn, G. M.; Bayless, A. V.; Ebetino, F. H. Inhibitory effects of bisphosphonates on growth of amoebae of the cellular slime mold *Dictyostelium discoideum*. J. Bone Miner. Res. 1994, 9, 1029-1039.

(37) van Beek, E. R.; Cohen, L. H.; Leroy, I. M.; Ebetino, F. H.; Löwik, C. W.; Papapoulos, S. E. Differentiating the mechanisms of antiresorptive action of nitrogen containing bisphosphonates. Bone 2003, 33, 805-11.

U.S. Pat. No. 5,583,122 by Benedict et al., issued Dec. 10, 1996; U.S. Pat. No. 6,562,974 by Cazer et al., issued May 13, 2003; U.S. Pat. No. 6,544,967 by Daifotis et al., issued Apr. 8, 2003; U.S. Pat. No. 6,410,520 by Cazer et al., issued Jun. 25, 2002; U.S. Pat. No. 6,372,728 by Ungell, issued Apr. 16, 2002; U.S. Pat. No. 6,638,920 by Thompson, issued Oct. 28, 2003; U.S. Pat. No. 4,777,163 by Bosies et al., issued Oct. 11, 1988; U.S. Pat. No. 4,939,130 by Jaeggi et al., issued Jul. 3, 1990 ('163 and '130 may be relevant to Zometa/zoledronate); U.S. Pat. No. 4,859,472 by Demmer et al., issued Aug. 22, 1989; U.S. Pat. No. 5,227,506 by Saari et al., issued Jul. 13, 1993; U.S. Pat. No. 6,753,324 by Jomaa, issued Jun. 22, 2004.

Alfer'ev, I. S.; Mikhalin, N. V., Reactions of vinylidenediphosphonic acid with nucleophiles. 5. Addition of heterocyclic amines and trimethylamine to vinylidenediphosphonic acid; August 1994, Russian Chemical Bulletin 44(8): 1528-1530 (translated from Izvestiya Akademii Nauk, Seriya Khimicheskaya 1995, 8, 1590-1592).

Alfer'ev IS et al., Izvestiay Akademii Nauk SSSR, Seriya Khimicheskaya, No. 12, pp.2802-2806, December 1983 [Bull. Acad. Sci. USSR, Div. Chem. Sci., 1983, 32:2515 (Engl. Transl.)].

Alfer'ev IS et al., Izv. Akad. Nauk SSSR, Ser. Khim., 1984:1122 [Bull. Acad. Sci. USSR, Div. Chem. Sci., 1984, 33:1031 (Engl. Transl.)].

International Publication No. WO03075741 by Wilder et al., published 18 Sep. 2003; International Publication No. WO2004024165 by Baulch-Brown et al., published 25 Mar. 2004; German Patent Publication DE19859668 by Hassan, published 30 Dec. 1999; International Publication No. WO2004050096 by Romagne et al., published 17 Jun. 2004.

Widler L, et al., Highly potent geminal bisphosphonates. From pamidronate disodium (Aredia) to zoledronic acid (Zometa), J Med Chem. Aug. 25, 2002;45(17):3721-38.

Green J R, Chemical and biological prerequisites for novel bisphosphonate molecules: results of comparative preclinical studies, Semin Oncol. Apr. 2001; 28(2 Suppl 6):4-10.

U.S. Pat. No. 4,711,880 by Stahl et al., issued Dec. 8, 1987 (Aredia/pamidronate); U.S. Pat. No. 4,621,077, U.S. Pat. No. 5,462,932, U.S. Pat. No. 5,994,329, U.S. Pat. No. 6,015,801, U.S. Pat. No. 6,225,294 (Fosamax/alendronate); U.S. Pat. No. 5,583,122, U.S. Pat. No. 6,096,342; U.S. Pat. No. 6,165,513 (Actonel/risedronate).

Wilhelm M et al., 2003, Gammadelta T cells for immune therapy of patients with lymphoid malignancies, Blood 102: 200-206.

Jagdev S P, Coleman R E, Shipman C M, Rostami H A, Croucher P I (2001); The bisphosphonate, zoledronic acid, induces apoptosis of breast cancer cells: evidence for synergy with paclitaxel. Br J Cancer 84:1126-1134.

U.S. Pat. No. 4,927,814 by Gall et al., issued May 22, 1990; U.S. Pat. No. 6,294,196 by Gabel et al., issued Sep. 25, 2001; U.S. Pat. No. 6,143,326 by Mockel, et al. issued Nov. 7, 2000 (ibandronate/Boniva®); U.S. Pat. No. 6,544, 967 by Daifotis, et al. Apr. 8, 2003.

Heidenreich et al., 2004. Ibandronate in metastatic bone pain, Semin. Oncol. 31(5 Suppl 10):67-72.

Gordon D H, 2005. Efficacy and safety of intravenous bisphosphonates for patients with breast cancer metastatic to bone: a review of randomized, double-blind, phase III trials, Clin Breast Cancer. 6(2):125-31.

De Cock et al., 2005. Cost-effectiveness of oral ibandronate versus IV zoledronic acid or IV pamidronate for bone metastases in patients receiving oral hormonal therapy for breast cancer in the United Kingdom. Clin. Ther. 27(8): 1295-310.

Sanders et al., Pyridinium-1-yl Bisphosphonates Are Potent Inhibitors of Farnesyl Diphosphate Synthase and Bone Resorption, J. Med. Chem. 2005, 48, 2957-296.

Kotsikorou Evangelia et al., Bisphosphonate Inhibition of the Exopolyphosphatase Activity of the Trypanosoma brucei Soluble Vacuolar Pyrophosphatase, J. Med. Chem. 2005, 48, 6128-6139.

The invention claimed is:

1. A compound having the formula CA1:

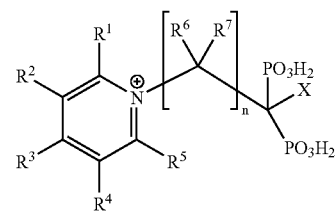

or a pharmaceutically acceptable salt thereof; wherein:

X is —OH, or a halogen;

n is 1, 2, or 3;

$R^1$-$R^5$, independently of one another are selected from the group consisting of a hydrogen, a halogen, a —CN, —OR, —COOR, —OCOOR, —COR, —CON(R)$_2$, —OCON(R)$_2$, —N(R)$_2$, —NO$_2$, —SR, —SO$_2$R, —SO$_2$N(R)$_2$ or —SOR group, an optionally substituted alkyl group, an optionally substituted alkenyl group, and an optionally substituted aryl group, where each R, is selected from H, an optionally substituted alkyl group and an optionally substituted aryl group, an optionally substituted acyl group; and $R^6$ and $R^7$, independently of each other are selected from the group consisting of a hydrogen, a halogen, a —N(R)$_2$, or —SR group, an optionally substituted alkyl group, an optionally substituted alkenyl group, an optionally substituted alkoxy group, and an optionally substituted aryl group, where each R, is selected from H, an optionally substituted alkyl group and an optionally substituted aryl group; and wherein $R^6$ and $R^7$ can together form a ring which may contain one or more double bonds.

2. The compound of claim 1 wherein X is OH, n=1, and $R^1$-$R^7$ are H.

3. The compound of claim 1 wherein X is the halogen and the halogen is selected from the group consisting of Cl or F.

4. The compound of claim 1 wherein X is Cl.

5. The compound of claim 1 wherein X is F.

6. A compound having the formula CA1:

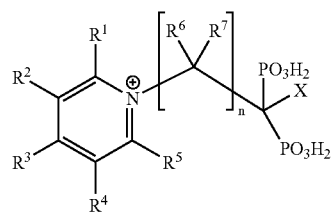

or a pharmaceutically acceptable salt thereof; wherein:

X is —OH;

n is 1, 2, or 3;

$R^1$-$R^5$, independently of one another are selected from the group consisting of a hydrogen, a halogen, a —CN, —OR, —COOR, —OCOOR, —COR, —CON(R)$_2$, —OCON(R)$_2$, —N(R)$_2$, —NO$_2$, —SR, —SO$_2$R, —SO$_2$N(R)$_2$ or —SOR group, an optionally substituted alkyl group, an optionally substituted alkenyl group, and an optionally substituted aryl group, where each R, is selected from H, an optionally substituted alkyl group and an optionally substituted aryl group, an optionally substituted acyl group; and $R^6$ and $R^7$, independently of each other are selected from the group consisting of a hydrogen, a halogen, a —N(R)$_2$, or —SR group, an optionally substituted alkyl group, an optionally substituted alkenyl group, an optionally substituted alkoxy group, and an optionally substituted aryl group, where each R, is selected from H, an optionally substituted alkyl group and an optionally substituted aryl group; and wherein $R^6$ and $R^7$ can together form a ring which may contain one or more double bonds.

7. A compound of selected from the group of compounds consisting of compounds 278, 297, 300, 335, 344, 359, 364, 398, 443-447, 449-452, 455-457, 459-462, 471, 478, 479, 484, 513, 520, 524, 534, 582, 583, 590, 591, 595, 600, 607, 612, 613, ZZ1 and pharmaceutically acceptable salts thereof, the chemical formulas of which compounds are:

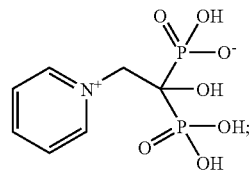
278

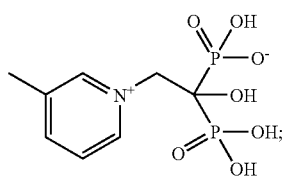
297

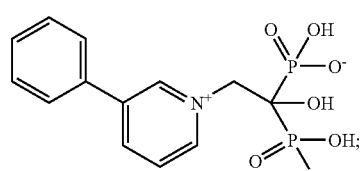
300

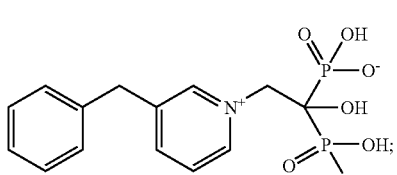
335

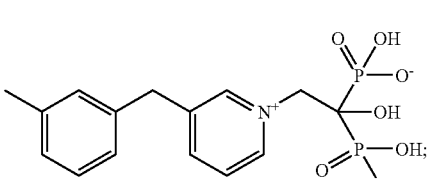
344

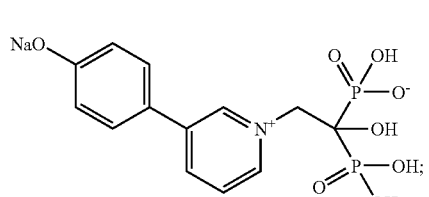
359

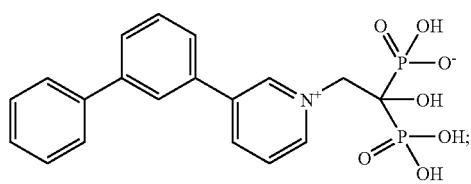
364

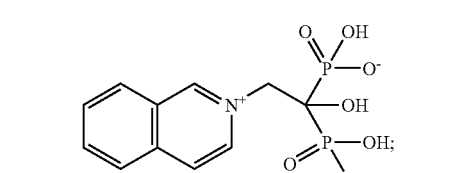
398

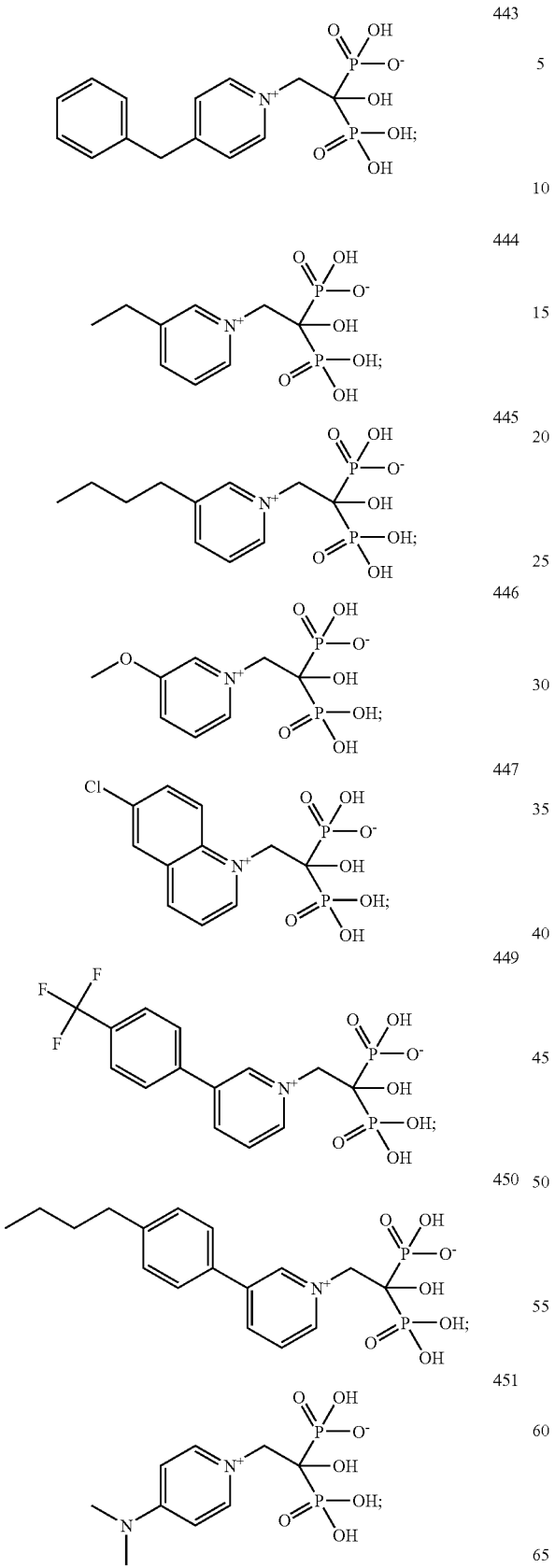
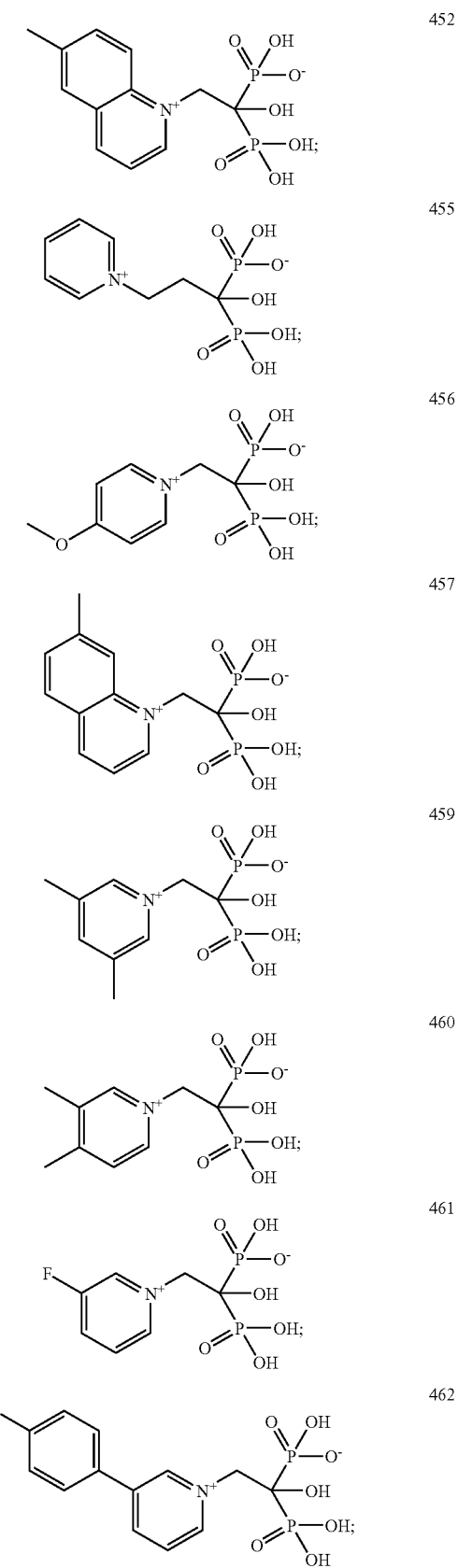

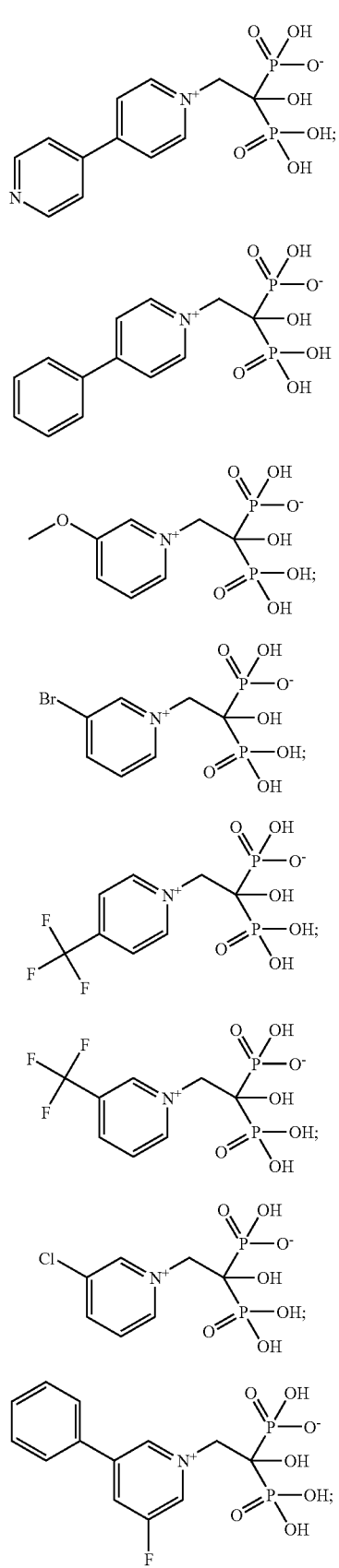
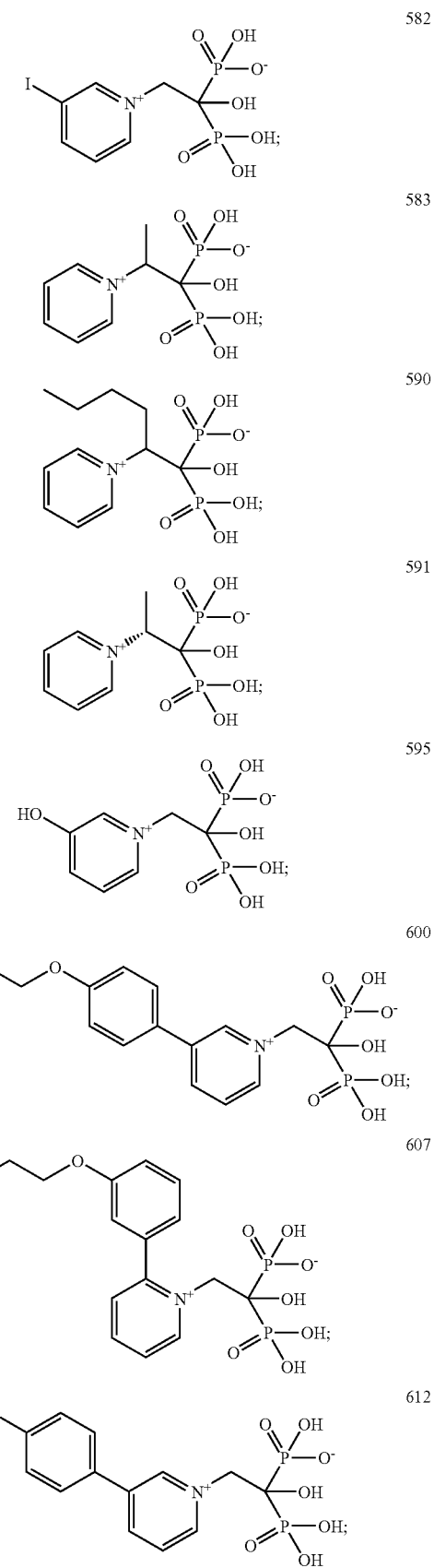

613

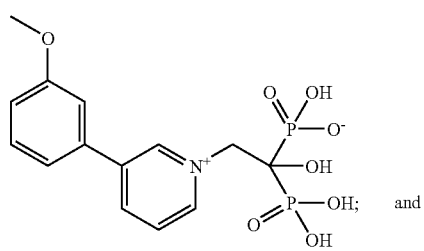

and

ZZ1

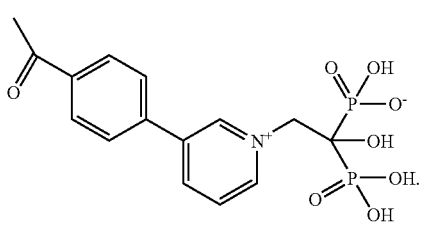

8. A compound of claim 1 selected from the group of compounds consisting of compounds 278, 297, 300, 335, 344, 359, 364, 444, 445, 446 and pharmaceutically acceptable salts thereof, the chemical formulas of which compounds are:

278

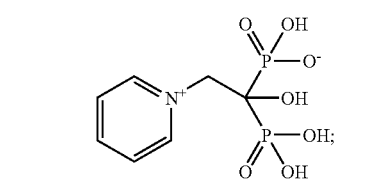

297

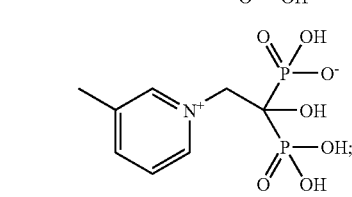

300

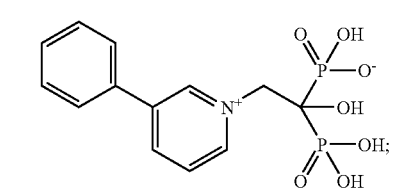

335

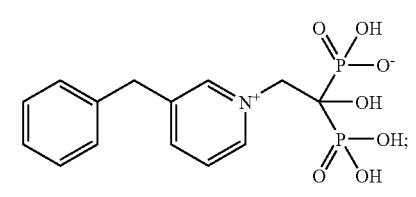

344

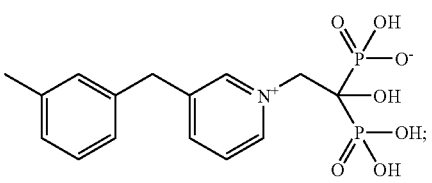

359

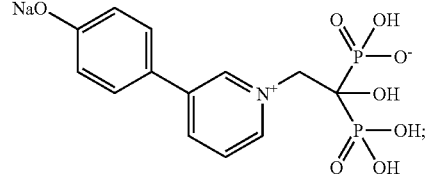

364

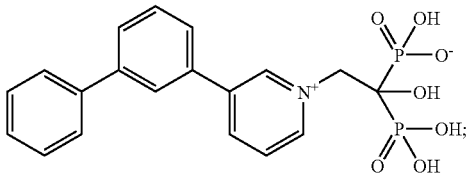

444

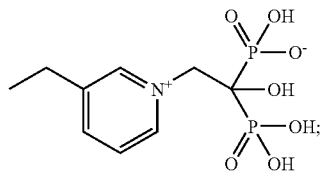

445

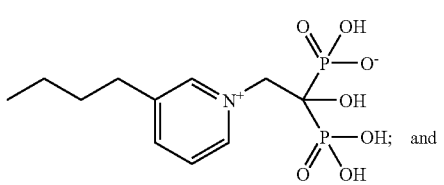

and

446

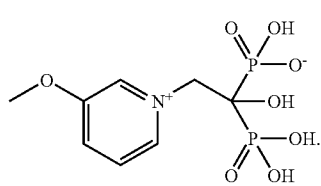

9. A compound of claim 1 selected from the group of compounds consisting of compounds 278, 297, 300, 444, 445, 461, 484 and pharmaceutically acceptable salts thereof, the chemical formulas of which compounds are:

278

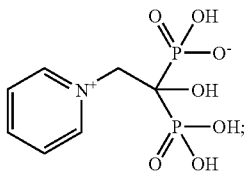

297

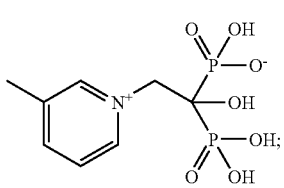

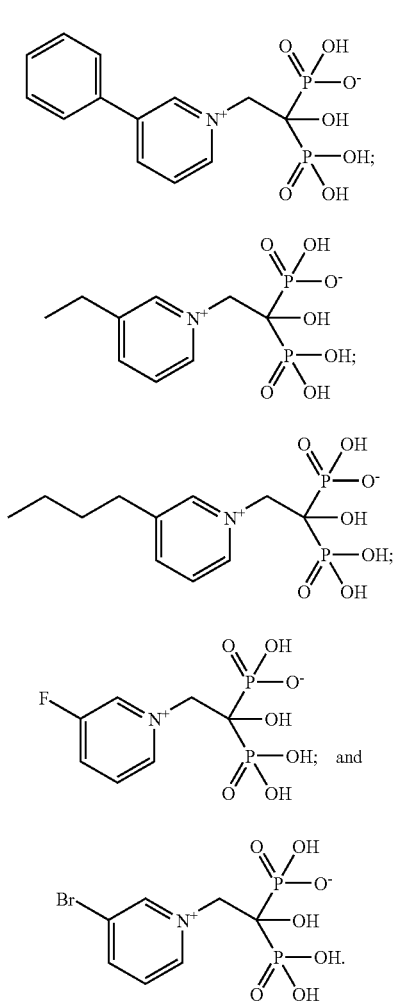
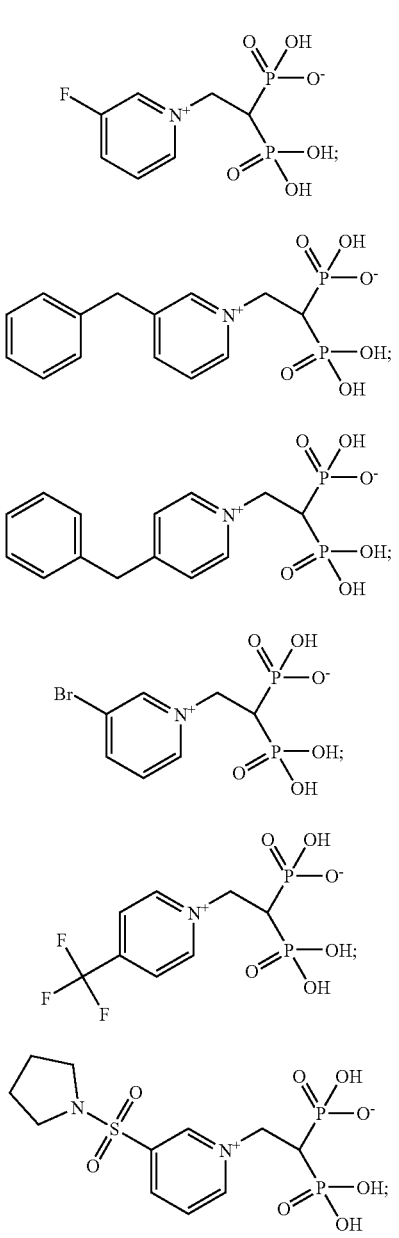
10. A compound selected from the group of compounds consisting of compounds 472, 476, 477, 480, 481, 483, 485, 502, 511, 521, 523, 526, 529-533, 542, 556, 577-579, 586, 588, 597-599, 601-605, 610 and pharmaceutically acceptable salts thereof, the chemical formulas of which compounds are:
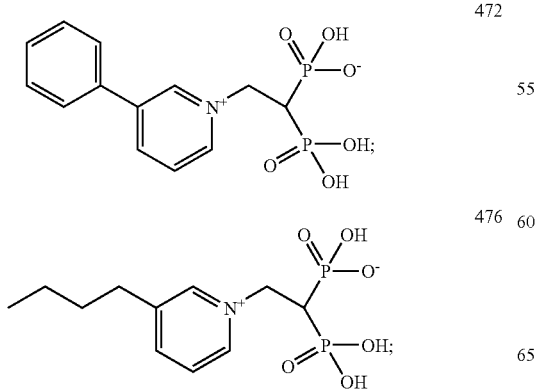

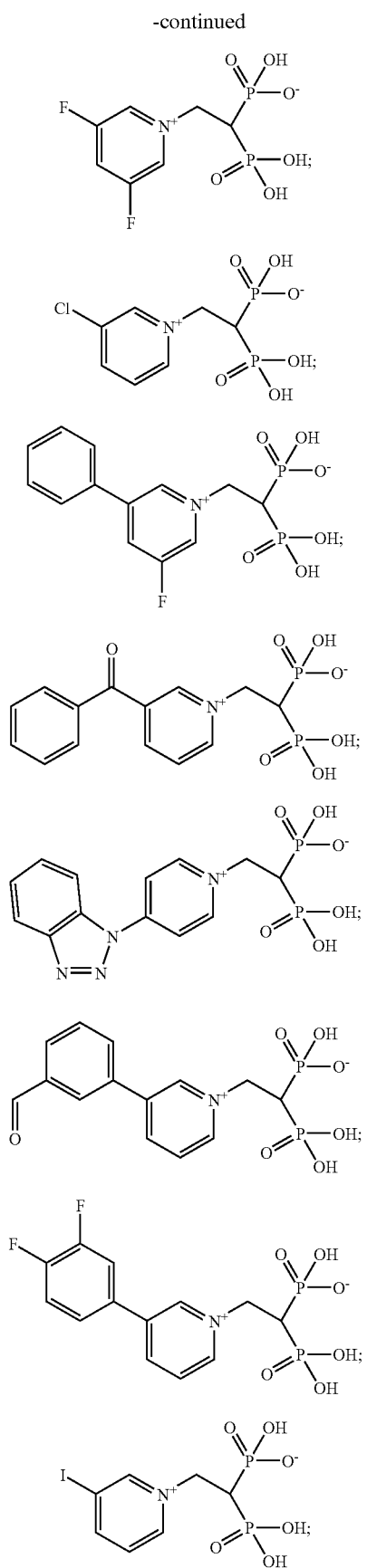
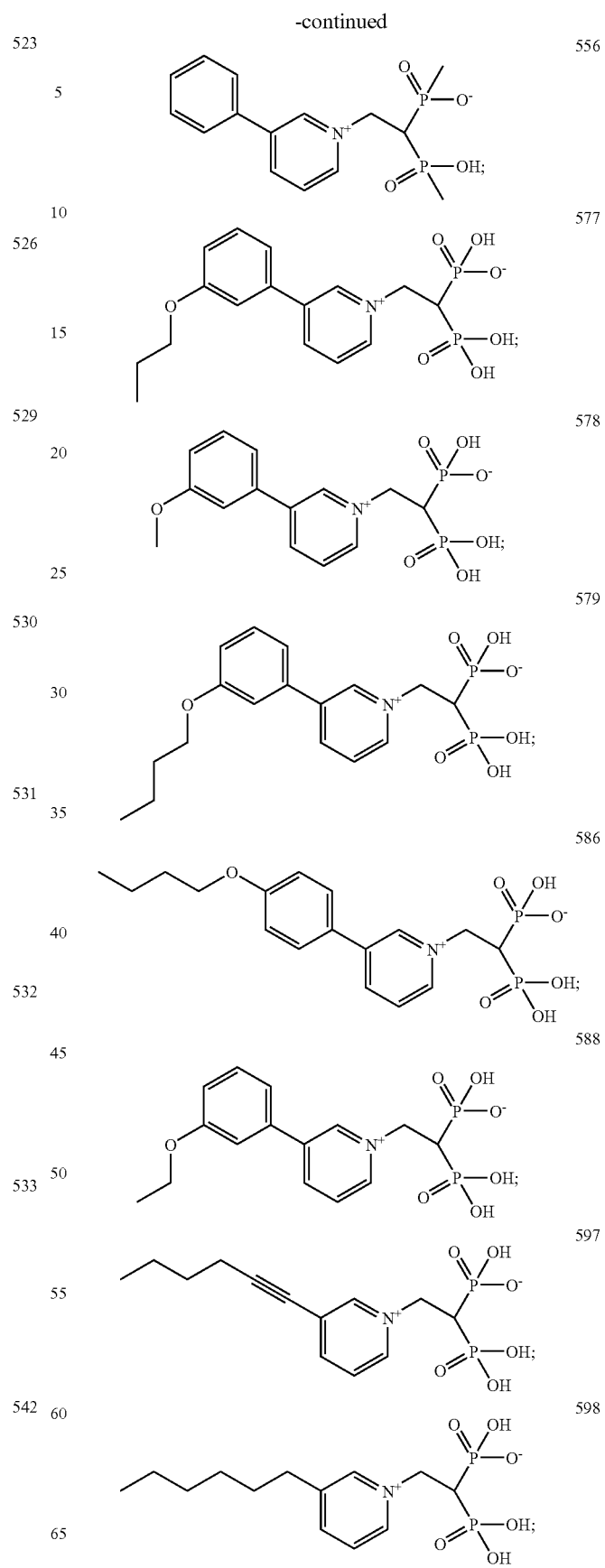

-continued
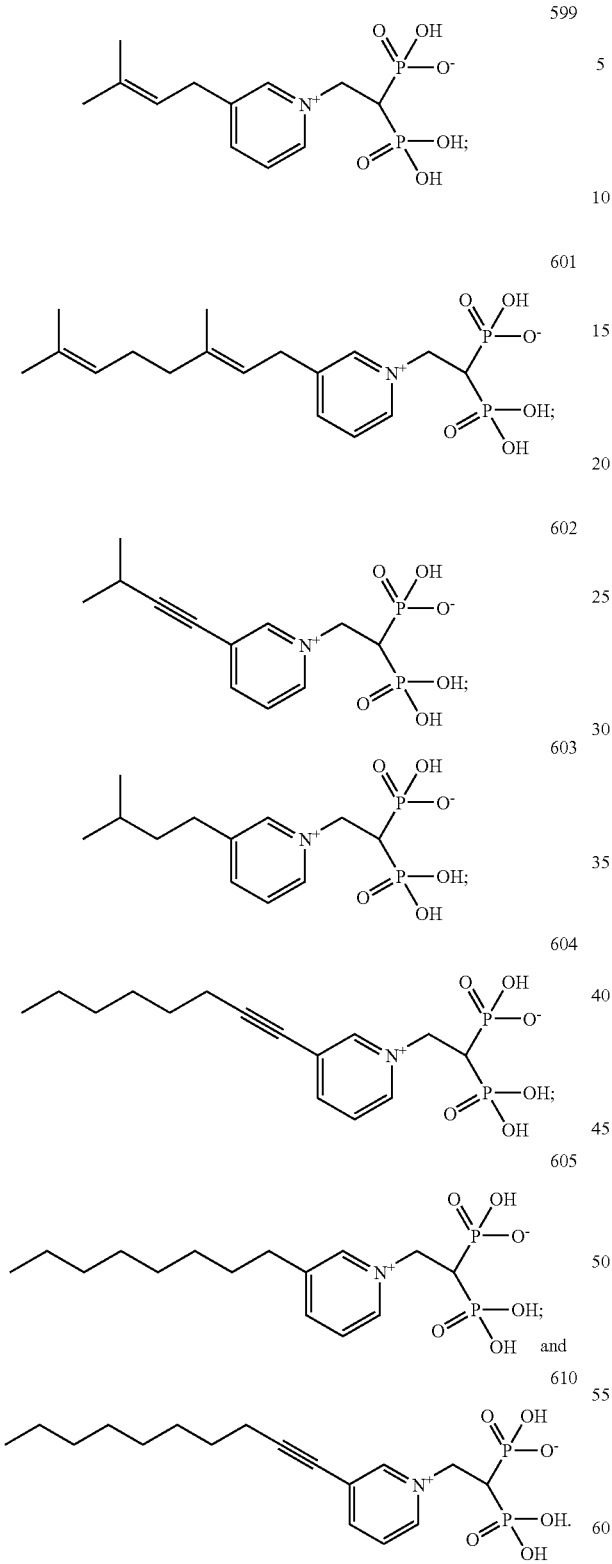
11. A compound of claim 10 selected from the group of compounds consisting of compounds 472, 476, 477, 483, and pharmaceutically acceptable salts thereof, the chemical formulas of which compounds are:
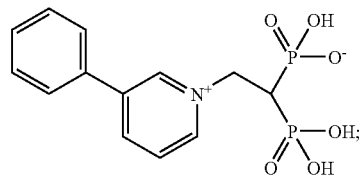
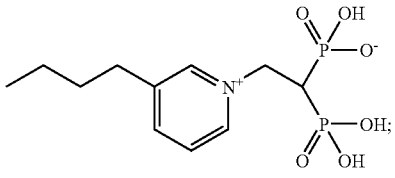
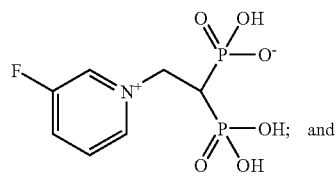
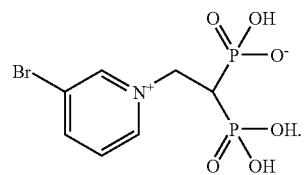
12. A compound of claim 10 selected from the group consisting of the compounds 476, 577-579, 586, 588, 597-599, 601-605, 610, and pharmaceutically acceptable salts thereof, the chemical formulas of which compounds are:
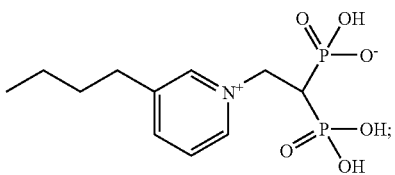
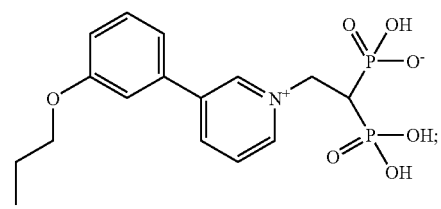
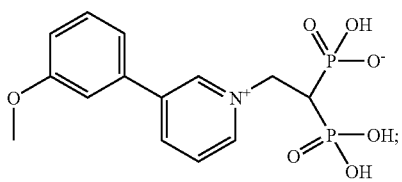

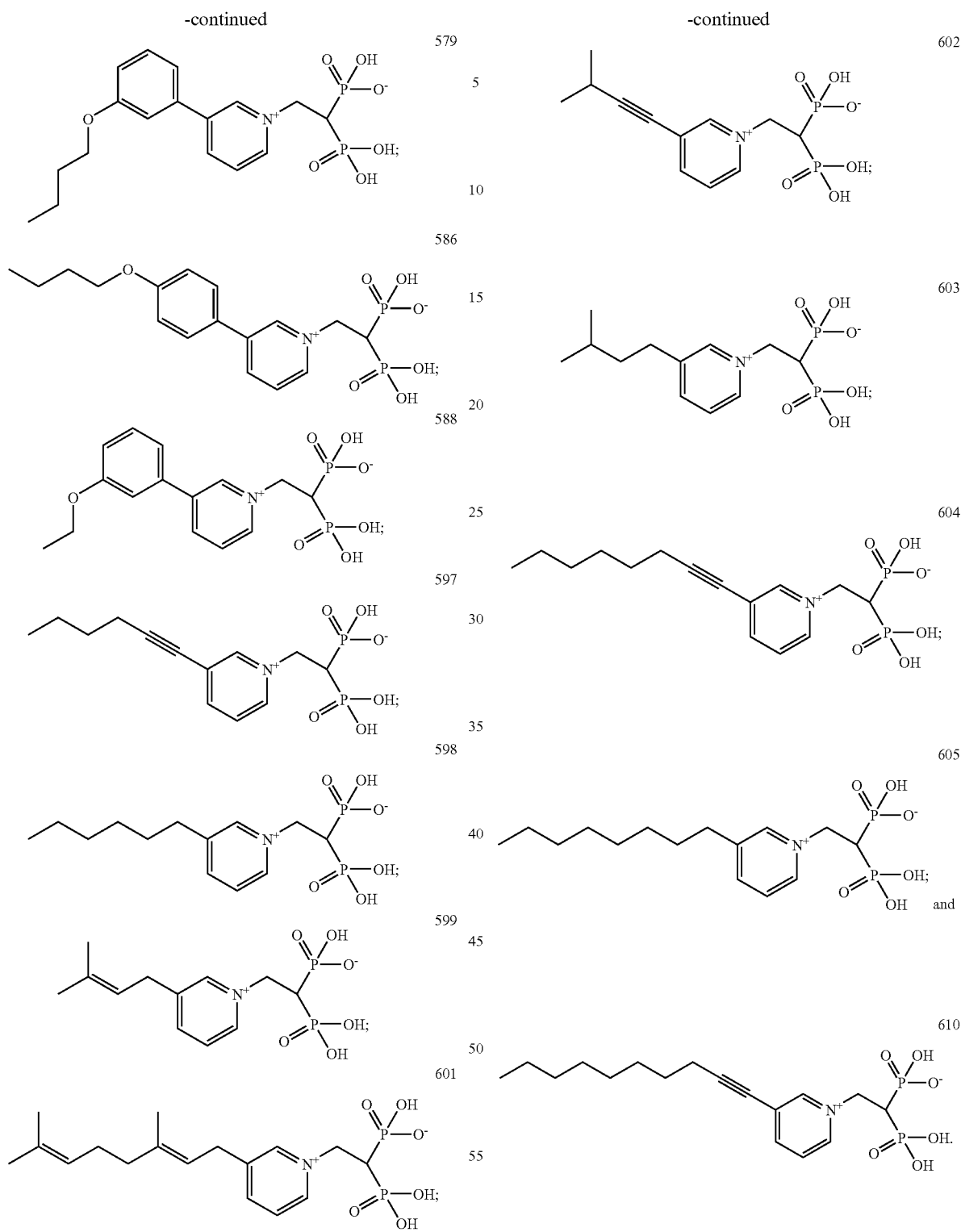

UNITED STATES PATENT AND TRADEMARK OFFICE
CERTIFICATE OF CORRECTION

| | | |
|---|---|---|
| PATENT NO. | : 7,358,361 B2 | Page 1 of 1 |
| APPLICATION NO. | : 11/245612 | |
| DATED | : April 15, 2008 | |
| INVENTOR(S) | : John M. Sanders et al. | |

It is certified that error appears in the above-identified patent and that said Letters Patent is hereby corrected as shown below:

On the Title Page

Item (54) Title, Line 1

Please replace "BIOPHOSPHONATE" with --BISPHONATE--.

Column 1, line 1, please replace "BIOPHOSPHONATE" with --BISPHOSPHONATE--.

Claim 7, Column 29, line 65, please replace "A compound of selected" with --A compound selected--.

Signed and Sealed this

Ninth Day of March, 2010

David J. Kappos
*Director of the United States Patent and Trademark Office*